US007320868B2

(12) United States Patent
Gertler et al.

(10) Patent No.: US 7,320,868 B2
(45) Date of Patent: Jan. 22, 2008

(54) LEPTIN BINDING DOMAIN COMPOSITIONS AND METHODS THERETO

(76) Inventors: Arieh Gertler, 11 Hagefen Str, Rehovot (IL) 76345; Radha Krishna, 3711 Summer Cove Ct., Friendswood, TX (US) 77546

( * ) Notice: Subject to any disclaimer, the term of this patent is extended or adjusted under 35 U.S.C. 154(b) by 282 days.

(21) Appl. No.: 10/803,459

(22) Filed: Mar. 19, 2004

(65) Prior Publication Data
US 2005/0209137 A1 Sep. 22, 2005

(51) Int. Cl.
*G01N 33/53* (2006.01)
*G01N 33/566* (2006.01)
*C12Q 1/00* (2006.01)
*C07K 17/00* (2006.01)
*C07K 16/00* (2006.01)
*C12N 5/06* (2006.01)

(52) U.S. Cl. .......................... 435/7.1; 435/4; 436/501; 530/350; 530/387.1

(58) Field of Classification Search ..................... None
See application file for complete search history.

(56) References Cited

U.S. PATENT DOCUMENTS

| 6,277,592 B1 | 8/2001 | Bidwell et al. |
| 6,297,027 B1 | 10/2001 | Spurlock |
| 6,492,178 B1 | 12/2002 | Pandian |
| 2002/0110857 A1 | 8/2002 | Spurlock |
| 2002/0127642 A1 | 9/2002 | Spurlock et al. |
| 2002/0137100 A1 | 9/2002 | Illmensee et al. |
| 2004/0038305 A1 | 2/2004 | Poston et al. |

FOREIGN PATENT DOCUMENTS

| WO | WO 01/30963 A2 | 10/1999 |
| WO | WO 2005/049655 A1 | 11/2003 |

OTHER PUBLICATIONS

Horev et al., Molecular cloning and properties of the chicken leptin-receptor (CLEPR) gene, 2000, Molecular and Cellular Endocrinology, vol. 162, p. 95-106.*
Kratzsch et al., A rapid, quantitative immunofunctional assay for measuring human leptin, 2002, Hormone Research, vol. 57, pp. 127-132.*
Sandowski et al., J. Biological Chemistry, Nov. 29, 2002, pp. 46304-46309, vol. 277 (48), USA.
Haniu et al., J. Biological Chemistry, Oct. 30, 1998, pp. 28691-28699, vol. 273 (44), USA.
Fong et al., Molecular Pharmacology, 1998, pp. 234-240, vol. 53, USA.
Gavrilova et al., J. Biological Chemistry, Nov. 28, 1997, pp. 30546-30551, vol. 272 (48), USA.
Liu et al., Endocrinology, 1997, pp. 3548-3554, vol. 138 (8), USA.
Devos et al., J. Biological Chemistry, Jul. 18, 1997, pp. 18304-18310, vol. 272 (29), USA.
Kratzsch et al., Hormone Research, 2002, pp. 127-132, vol. 57, USA.
Dridi et al., Am. J. Physio. Endocrinol. Metab., 2000, pp. E116-E123, vol. 279, USA.
Wu et al., J. Clinical Endocrinol. Metab., 2002, pp. 2931-2939, vol. 87 (6), USA.
Baumgartner et al., J. Biological Chemistry, Nov. 18, 1994, pp. 29094-29101, vol. 269 (46), USA.
Sinha et al., J. Clinical Investigation, Sep. 1996, pp. 1277-1282, vol. 98 (6), USA.
Maamra et al., Endocrinology, 2001, pp. 4389-4393, vol. 142 (10), USA.
Raver et al., Experimental Biology 2003 Meeting Abstract, Apr. 2003, Abstract No. 571.1, USA.
Ohkubo et al., Biochimica et Biophysica Acta, 2000, pp. 303-308, vol. 1491, USA.
Horev et al., Molecular and Cellular Endocrinology, 2000, pp. 95-106, vol. 162, USA.
Tartaglia et al., Cell, Dec. 29, 1995, pp. 1263-1272, vol. 83, USA.
Takaya et al., Biochemical and Biophysical Research Communications, 1996, pp. 75-83, vol. 225, USA.
Henson et al., Biology of Reproduction, 2000, pp. 1219-1228, vol. 63, USA.
Tartaglia, J. Biological Chemistry, Mar. 7, 1997, pp. 6093-6096, vol. 272 (10), USA.
Janeckova, Physiol. Res., 2001, pp. 4430459, vol. 50, USA.
Bradley et al., Recent Prog. Horm. Res., 2001, pp. 329-358, vol. 56, USA.
Huang et al., Cell Research, 2000, pp. 81-92, vol. 10, USA.
Houseknecht et al., Diabetes, 1996, pp. 1638-1643, vol. 45 (11), USA.
Luoh et al., J. Molecular Endocrinology, 1997, pp. 77-85, Abstract, vol. 18 (1), USA.
Taouis et al., Gene, Feb. 22, 1998, pp. 239-242, vol. 208 (2), USA.
Rock et al., Horm. Metab. Res., Dec. 1996, pp. 748-750, vol. 28 (12), USA.
Gertler et al., FEBS Lett., Jan. 30, 1996, pp. 137-140, vol. 422 (2), USA.

(Continued)

*Primary Examiner*—Bridget E. Bunner
*Assistant Examiner*—Ian Dang
(74) *Attorney, Agent, or Firm*—Holly O. Soehnge

(57) ABSTRACT

The present invention provides compositions and methods relating to avian leptin receptor binding domains. The present invention demonstrates that these compositions are useful for detecting the presence of leptin in a sample and distinguishing free leptin from bound leptin in multiple species. Methods and kits are presented for determining free leptin in a sample from an individual by assaying a sample for the binding of leptin to an avian leptin receptor binding domain, and detecting the bound leptin by using a labeled anti-leptin antibody.

12 Claims, 15 Drawing Sheets

OTHER PUBLICATIONS

Raver et al., Gen. Comp. Endocrinol., Mar. 2002, pp. 52-58, Abstract, vol. 126 (1), USA.

Taouis et al., Domest. Anim. Endocrinol., Nov. 2001, pp. 319-327, Abstract, vol. 21 (4), USA.

Raver et al., Protein Expr. Purif., Jun. 2000, pp. 30-40, Abstract, vol. 19 (1), USA.

Raver et al., Protein Expr. Purif., Dec. 1998, pp. 403-408, Abstract, vol. 14 (3), USA.

Richards et al., Comp. Biochem. Physiol. B. Biochem. Mol. Biol., Dec. 2003, pp. 833-847, Abstract, vol. 136 (4), USA.

Gonzalez et al., Endocrine, Jul. 2003, pp. 185-195, vol. 21 (2), USA.

Yiannakouris et al., J. Clin. Endocrinol. & Metab., 2001, pp. 4434-4439, vol. 86 (9), USA.

Kiess et al., J. Clin. Endocrinol. & Metab., 2001, pp. 4472-4479, vol. 86 (9), USA.

* cited by examiner

Hormone chLBD(mole : mole)

LEPTIN BINDING DOMAIN COMPOSITIONS AND METHODS THERETO

BACKGROUND OF THE INVENTION

1. Field of the Invention

The present invention relates generally to leptin binding domain compositions and methods thereto. The compositions are useful for detecting the presence of leptin in a sample and distinguishing free leptin from bound leptin in multiple species. More specifically, the present invention relates to methods for determining free leptin in a sample from an individual by assaying a sample for the binding of leptin to an avian leptin receptor binding domain, and detecting the bound leptin by using a labeled anti-leptin antibody.

2. Description of the Related Art

Human leptin is a 16 kDa, 146 amino acid residue, non-glycosylated polypeptide that was described based on the genetic mapping of a recessive mutation that caused severe obesity in mice (1-2). Abolished transcription or production of an inactive obesity (ob) gene product was found to be responsible for producing the obese (ob/ob) mouse, which is characterized by severe obesity, hyperphagia, hyperglycemia, hyperinsulinemia and insulin resistance, hypothermia, and infertility (3-5). The obesity gene product, later known as leptin, is produced by the adipose tissue across a wide range of animal species (1, 2) and shows high interspecies conservation, with the human leptin sharing up to 84% and 87% homology with rat and mouse leptin, respectively (1, 6). Crossing the blood-brain barrier (7), circulating leptin is believed to convey vital information to the brain regarding the level of body fat and energy stores and activate the hypothalamic centers that regulate food intake and energy expenditure (3, 4, 7, 8). A number of recent reports have proposed adipose tissue as an important endocrine gland, and have identified leptin as a pleiotrophic hormone affecting many different organs and tissues in the body (9-11). In addition to regulating fat metabolism, involvement of leptin in pathophysiology of multiple endocrine feedback loops, including reproductive, hematopoiesis, and adrenal cortex function, as well as immune system function, have been reported (8, 9, 11-13).

The effects of leptin on various functions may be mediated centrally via changes in hypothalamic neuropeptide Y expression, which in turn regulates the secretion of gonadotropic hormones (36) and food intake (37). Metabolic changes induced by alterations in food intake affect various hormone systems indirectly. In addition to its systemic effects, direct peripheral leptin actions have been demonstrated in several target tissues. Thus, leptin has been shown to modulate insulin activity in hepatocytes in vitro (38). Leptin modulates ovarian steroidogenesis in vitro (39, 40) and affects angiogenesis, acting in some tissues as a positive angiogenic factor (41), whereas it is angiostatic in adipose tissues (42). In rat ovary, leptin attenuates apoptosis and thus enhances sexual maturation (43). Leptin also regulates several functions in the pituitary cells (44).

Leptin circulates in serum as a free form or bound to leptin-binding proteins, such as a soluble form of leptin-binding receptor (35). The majority of leptin is in the bound form in lean individuals, but in the free form in obese individuals (35). In addition, leptin levels are also influenced by the stage of puberty and gender in both adults and children. Blood leptin levels are about 2-3 fold higher in men than in women (3, 4, 15-18); its secretion is pulsatile (19) and follows a circadian rhythm, with the highest levels achieved during the night (19, 20). Obesity in man, in contrast to obesity in mice, is associated with a significant increase in circulating leptin levels (14). Fat mass is the main determinant of leptin to the extent that its circulating levels are exponentially correlated with body mass index (BMI) and percent body fat (2-4, 14). The high sensitivity of leptin to changes in body fat is responsible for the observed wide variations in plasma leptin, which could range from 0.03 to over 100 ng/mL (15-18). Studies have indicated that loss of body fat decreases serum leptin levels, while an increase in body fat increases leptin levels; these observations suggest that the body's adaptive response to low serum leptin differs from the response to high leptin levels in a way that is characteristic for obesity (35).

Recombinant leptins from several farm animals, such as sheep (45), chicken (46), cow, pig (47), and humans (48) have been prepared. A variety of in vivo experiments performed with leptin-deficient ob/ob and normal mice (49-51), as well as with chicken and sheep (52-54), indicate that administration of leptin by direct intraventricular, intramuscular, or intraperitoneal injections leads to a remarkable decrease in food intake and subsequent weight loss. The main target of leptin's action is located in the brain, and as leptin is produced in adipose tissue, it has to be transferred through the blood-brain barrier. This transfer is mediated mainly through the short form of the leptin receptor located in the choroid plexus (55, 56). The leptin receptor is a member of the cytokine family of receptors and is responsible for mediating the biological activity of leptin (3, 4). In humans, four different mRNA splice variants of the leptin receptor have been so far identified (3, 4). Accordingly, secreted leptin may circulate in both free (unbound) as well as in complex forms bound to a number of different binding proteins. The latter reportedly includes a soluble splice variant of the receptor that has no transmembrane domain as well as soluble leptin receptor generated by the proteolytic cleavage of the membrane-anchored receptors and possibly other unidentified leptin binding proteins (3, 4, 22-23). Although the nature as well as biological importance of leptin association with binding proteins has not been fully defined, recent evidence has proposed a distinct role for the free and bound leptin (24). In addition, leptin association with binding proteins is thought to increase leptin bioavailability and half-life as well as possibly contributing to the state of leptin resistance (2, 3, 4, 19). As the balance of free and complex leptin is influenced by a complex array of variables, including several hormones and growth factors (3, 4), accurate determination of leptin sub-fractions could be of significant value in advancing our understanding of pathophysiology and potential diagnostics and therapeutic (10) applications of leptin.

Progress in leptin research was complemented by the discovery and cloning of the leptin receptor (3, 4, 21). While polynucleotides and polypeptides of chicken leptin receptor are reportedly provided in Horev, et al. (57) and WO 01/30963, the particular binding domain for the avian species was not provided. A citation of exons 9 and 10 by Fong (58) is in reference to the mammalian genes of humans and mice. WO 01/30963 reports only a 49-50% sequence similarity between those species and the chicken receptor amino acid sequences.

Continued progress in leptin research has also been aided by development of various methodologies for functional as well as clinical investigations of leptin (3, 4, 10). Currently, immunoassays are the method of choice for leptin quantification in serum and other biological fluids. The initial immunoassays, based on competitive principles (2, 25), have been largely replaced with non-competitive, non-isotopic, methodologies (26), which have the analytical performance advantages as well as avoiding the draw backs of radioactive labels. These immunoassays do not completely distinguish between the various circulating leptin forms (e.g., free vs complex, vs total) (26). Given the differential response of free and bound leptin to caloric intake, obesity, and other hormones as well as their potentially distinct pathophysiological roles (3, 4, 24), development of methodologies for specific determinations of free or complex leptin forms would be of significant value. In this context, a conventional, one-step, enzyme-linked immunosorbent assay (ELISA) for free leptin has been recently described (27). Development of a functional bioassay for free leptin has been also reported (28), but the methodology is relatively cumbersome and expensive for routine and large-scale applications.

SUMMARY OF THE INVENTION

This invention relates to methods and assays for the detection of free leptin levels in a sample from an individual. Data is presented that demonstrates the ability of avian or chicken leptin binding domain to bind effectively to leptin from multiple species.

We have recently designed and produced a recombinant leptin binding protein based on leptin receptor binding domain sequences expressed in chicken. Production of the chicken leptin binding protein domain (CLBD) was based on considerations of its potential diagnostic and/or therapeutic value, which was in turn grounded on structural and functional similarities that exists among leptin and leptin receptors in various species (1-4, 6). Recognizing the importance of a more specific approach to free leptin determination, we recently embarked on a systematic evaluation of CLBD. The present application provides the first interspecies combination of a non-immunological solid-phase binder (CLBD) with an immunological detection reagent (goat anti-leptin antibody) for specific determination of free leptin. The methodology is applicable for use in multiple animal species, based on the cross-reacting nature of the various binding reagents. The Free Leptin Receptor-Mediated Enzyme-Linked Immunoassay (RMEIA) is based on a receptor/antibody assay configuration, which is highly compatible with small as well as large-scale manual and/or fully automated applications.

The present inventors describe herein subcloning of an avian subdomain, its expression in a prokaryotic host, and its subsequent purification and characterization. Further, the present invention provides a leptin binding domain protein having a sufficient binding affinity for human leptin that the binding domain may be used as an antibody mimic in an immunoassay for leptin.

In one embodiment of the present invention, there is provided a composition comprising an avian leptin receptor binding domain having an amino acid sequence SEQ ID NO: 8 bound in a protein complex to a leptin protein. As demonstrated herein, the chicken leptin receptor binding domain binds to leptin at the same site as the mammalian leptin receptor binding domain, and therefore the avian domain is an agent for competition binding to human leptin in the presence of the human domain, and the avian domain is provided for binding free leptin in biological fluids such as plasma and serum.

Another embodiment of the present invention provides a method for detecting a level of free leptin in a sample from an individual, comprising contacting the sample with an avian leptin receptor binding domain of SEQ ID NO:8 for a time sufficient to allow binding between the free leptin and the leptin receptor binding domain to form a bound complex, wherein said receptor binding domain is bound to a solid phase; washing the solid phase with a first wash buffer; contacting the solid phase with an antibody having binding specificity to leptin, wherein said antibody is coupled with a detectable label; washing the solid phase with a second wash buffer, and detecting said label remaining with said solid phase, thus detecting the level of free leptin in the sample.

In another embodiment of the present invention, there is provided a kit for an assay of a level of free leptin in a sample from an individual, comprising an avian leptin receptor binding domain comprising SEQ ID No. 8, wherein said domain is bound to a solid phase; an antibody having binding specificity for leptin; and a detectable label coupled with the antibody, wherein the free leptin in the sample binds to the avian leptin receptor binding domain and the antibody binds to the free leptin, thus allowing specific detection of the free leptin in the sample.

In yet another embodiment of the present invention, there is provided a method of assaying a test compound for agonist or antagonist activity for the binding of a leptin with a leptin binding domain comprises a) measuring a level of interaction between the avian leptin receptor binding domain and the mammalian leptin in the absence of the test compound; b) measuring a level of interaction between the avian leptin receptor binding domain and the mammalian leptin in the presence of the test compound, wherein when the level measured in step b) is greater than the level in step a), the test compound has agonist activity, and wherein when the level measured in step b) is less than the level in step a), the test compound has antagonist activity.

Advantages to using avian leptin receptor binding domain for detection rather than a leptin receptor specific antibody include use of a much smaller molecule for detection. An additional advantage of the present invention is that using avian or chicken leptin binding domain for detection allows assaying for free leptin levels in multiple species using the same assay.

Other and further aspects, features, benefits, and advantages of the present invention will be apparent from the following description of the presently preferred embodiments of the invention given for the purpose of disclosure.

BRIEF DESCRIPTION OF THE DRAWINGS

The following drawings form part of the present specification and are included to further demonstrate certain aspects of the present invention, so that the matter in which the above-recited features, advantages, and objects of the invention, as well as others which will become clear, are attained and can be understood in detail. The invention may be better understood by reference to one or more of these drawings in combination with the detailed description of the specific embodiments presented herein. It is to be noted, however, that the appended drawings illustrate preferred embodiments of the invention and therefore are not to be considered limiting in their scope.

DETAILED DESCRIPTION OF THE PREFERRED EMBODIMENTS

Figure 1:
FIG. 1 illustrates a SDS-PAGE analysis of recombinant hLBD on a 15% gel. Lane 1, molecular mass markers (172, 111, 79.6, 61.3 (the strongest band), 49, 36.4, 24.7, 19.2, 13.1, 9.3 kDa); lane 2, IPTG-induced bacteria; lane 3, inclusion bodies; lanes 4-6, pooled 100, 125, and 150 mM NaCl eluates (see legend to FIG. 2) following pretreatment with reducing agent; lanes 8-10, the same but without pretreatment with reducing agent; lane 7, empty.

In one aspect, the present invention is directed to a composition comprising an avian leptin receptor binding domain having an amino acid sequence SEQ ID NO: 8 bound in a complex to a leptin protein. A representative example of avian leptin receptor binding domain is chicken leptin receptor binding domain. In another aspect, the leptin protein is mammalian leptin, wherein the mammalian leptin may be human, rat, mouse, ovine, porcine, or bovine leptin.

Another aspect of the present invention is directed to a method for detecting a level of free leptin in a sample from an individual, comprising contacting the sample with an avian leptin receptor binding domain of SEQ ID NO:8 for a time sufficient to allow binding between the free leptin and the leptin receptor binding domain to form a bound complex, wherein said receptor binding domain is bound to a solid phase; washing the solid phase with a first wash buffer, contacting the solid phase with an antibody having binding specificity to leptin, wherein said antibody is coupled with a detectable label; washing the solid phase with a second wash buffer, and detecting said label remaining with said solid phase, thus detecting the level of free leptin in the sample. Representative examples of the detectable label include a label that is radiolabeled, chemiluminescent, electroluminescent, fluorescent, enzyme-labeled, or bioluminescent. In a preferred embodiment, the solid phase is a micro-titre well plate. In one aspect of the present invention, the avian leptin receptor binding domain is chicken leptin receptor binding domain. In yet another aspect, the individual is a mammal, wherein said mammal may possibly be human, rat, mouse, ovine, porcine, or bovine. In one embodiment, the sample is a human serum or plasma sample. In another embodiment, the individual has a condition or a disease related to the level of free leptin in the sample.

Another preferred embodiment of the present invention is directed to a kit for an assay of a level of free leptin in a sample from an individual, comprising an avian leptin receptor binding domain comprising SEQ ID No. 8, wherein said domain is bound to a solid phase; an antibody having binding specificity for leptin; and a detectable label coupled with the antibody, wherein the free leptin in the sample binds to the avian leptin receptor binding domain and the antibody binds to the free leptin, thus allowing specific detection of the free leptin in the sample. Another aspect provides that the avian leptin receptor binding domain is chicken leptin receptor binding domain. In another aspect, the individual is a mammal; representative examples include mammals that are human, rat, mouse, ovine, porcine, or bovine. Other aspects include a sample that is a human serum or plasma sample, and wherein the solid phase is a micro-titre well plate. The detectable label may be radiolabeled, chemiluminescent, electroluminescent, fluorescent, enzyme-labeled, or bioluminescent.

Another embodiment of the present invention provides a method of assaying a test compound for agonist or antagonist activity for an avian leptin receptor binding domain-leptin complex, comprising a) measuring a level of interaction between the avian leptin receptor binding domain and the mammalian leptin in the absence of the test compound; and b) measuring a level of interaction between the avian leptin receptor binding domain and the mammalian leptin in the presence of the test compound, wherein when the level measured in step b) is greater than the level in step a), the test compound has agonist activity, and wherein when the level measured in step b) is less than the level in step a), the test compound has antagonist activity.

The present invention provides recombinant leptin receptor binding domains for use in the elucidation of leptin-leptin receptor interactions, for screening assays, and for diagnostic assays. A recombinant ~200 amino acid fragment of the ECD of human and chicken leptin receptors were shown to possess the ability to bind human, ovine and chicken leptins and to form stable 1:1 complexes.

The chicken leptin receptor binding domain exclusively binds to free leptin even when it is in the presence in a mixture of free-leptin and bound leptin (such as in an in vivo condition) because of the exclusive specificity to the binding domain of leptin.

Generally, a protein such as an polyclonal or monoclonal antibody or a binding domain of leptin receptor may be labeled with a detectable substance and the protein detected or localized based upon the presence of the detectable substance. Examples of detectable substances include, but are not limited to, radioisotopes (e.g., $^{3}H$, $^{14}C$, $^{35}S$, $^{125}I$, $^{131}I$), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels may be attached via spacer arms of various lengths to reduce potential steric hindrance. Proteins may also be coupled to electron dense substances, such as ferritin or colloidal gold, which are readily visualised by electron microscopy.

Indirect methods may be employed in which a primary antigen-antibody reaction is amplified by the introduction of a second antibody, having specificity for the antibody reactive against the primary antigen. For example, if an antibody having specificity against a binding domain is a rabbit IgG antibody, the second antibody may be goat anti-rabbit gammaglobulin labeled with a detectable substance as described herein.

Where a radioactive label is used as a detectable substance, the protein is localized by radioautography. The results of radioautography may be quantitated by determining the density of particles in the radioautographs by various optical methods, or by counting the grains.

For certain assays of the present invention, the leptin receptor binding domain may be attached to a solid support. By "solid support" is meant a non-aqueous matrix to which the domain protein of the present invention can adhere. Examples of solid supports include those formed partially or entirely of glass (e.g., controlled pore glass), polysaccharides (e.g., agarose), polyacrylamides, polystyrene, polyvinyl alcohol or silicones. The solid phase may comprise the well of an assay plate or a purification column, for example.

By an "antagonist" of leptin-binding domain interaction is meant an agent having inhibitory activity for the binding of leptin and a leptin receptor binding domain. The binding may be inhibited by an effect on the interaction between leptin and binding domain, or by an effect on leptin or binding domain that affects the interaction between leptin and binding domain.

By an "agonist" of leptin-binding domain interaction is meant an agent having enhancing or stimulatory activity for the binding of the leptin-binding domain complex. The binding may be stimulated by an effect on the interaction between leptin and binding domain or by an effect on leptin or binding domain that affects the interaction between leptin and binding domain. Identification of an antagonist or an agonist is made by allowing leptin and binding domain to interact in the presence of a test agent. A decrease or increase in leptin-binding domain interaction relative to the interaction when the test agent is absent indicates that the test agent has an effect on the binding interaction.

In leptin-binding domain protein compositions of the present invention, conservative amino acid substitutions, such as Glu/Asp, Val/Ile, Ser/Thr, Arg/Lys and Gln/Asn, would be considered equivalent since the chemical similarity of these pairs of amino acid residues would be expected to result in functional equivalency. Amino acid substitutions that conserve the biological function of the leptin-binding domain would conserve such properties as hydrophobicity, hydrophilicity, side-chain charge, or size. Functional equivalency is determined by the interaction of the equivalent bound complex as compared to the native bound complex. Included within the scope of the invention are complexes of leptin-binding domain, derivatives, or analogs thereof, e.g., by glycosylation, acetylation, phosphorylation, amidation, fatty acylation, sulfation, derivatization by known protecting/blocking groups, proteolytic cleavage, linkage to an antibody molecule or other cellular ligand, or the like.

By "free" leptin is meant leptin that is not bound to leptin-binding proteins. By "bound" leptin is meant leptin that is bound to one or more leptin-binding proteins, including but not limited to the soluble form of leptin-binding receptor.

The following examples are given for the purpose of illustrating various embodiments of the invention and are not meant to limit the present invention in any fashion.

EXAMPLE 1

Purification and Characterization of Leptin Receptor Binding Domain

Materials—Ovine leptin (fraction SP), chicken leptin, and human leptin (hLEP) were prepared as described (Gertler, A. et al. (1998) *FEBS Lett.* 442, 137-140; Raver, N. et al (1998) *Protein Expression Purif.* 14, 403-408; Raver, N. et al; (2002) *Gen. Comp. Endocrinol.* 126, 52-58); pET29a expression vector was purchased from Novogene Inc. (Madison, Wis.). Restriction enzymes used in the molecular biology experiments were from Fermentas (Vilnius, Lithuania) and New England Biolabs (Beverly, Mass.). DNA primers were ordered from Invitrogen. Lysozyme, urea, arginine, radioimmunoassay-grade bovine serum albumin, Triton X-100, RPMI 1640 medium, interleukin-3 (IL-3), isopropyl β-D-thiogalactopyranoside (IPTG), and 3-(4,5-dimethylthiazol-2-yl)-2,5-diphenyltetrazolium bromide (thiazolyl blue) were purchased from Sigma, fetal calf serum was from Biolab Co. (Jerusalem, Israel), and Superdex™75 HR 10/30 column, Q-Sepharose, and SP-Sepharose (fast flow) were from Amersham Biosciences. A research-grade CM5 sensor chip, N-hydroxysuccinimide, N-ethyl-N' (3-dimethylaminopropyl)-carbodiimide hydrochloride, ethanolamine hydrochloride, and HBS-EP running buffer (10 mM Hepes, 150 mM NaCl, 3.4 mM EDTA, and 0.005% (v/v) surfactant P20, pH 7.4) were purchased from Biacore, AB (Uppsala, Sweden). All other chemicals were of analytical grade.

Preparation of LBD Expression Plasmid—A DNA insert encoding the LBD fragment, consisting of amino acids 428-635 of the human leptin receptor (SEQ ID NO:1 provides the nucleotide sequence and SEQ ID NO:2 provides the amino acid sequence), was prepared by PCR using the following primers: the 5'-sense primer, 5'-GGAATTC CATATGATTGATGTCAATATCAATATCTC-3' (SEQ ID NO:3) containing an NdeI restriction site (underlined) and the antisense 3'-end primer, 5'-CATAGG AAGCTTTCAATCCATGACAACTGTGTAGGCTGG-3' (SEQ ID NO:4) containing a stop codon (bold letters) followed by a HindIII site (underlined). The resulted PCR product was cloned into the pGEM-T vector, sequenced to ensure lack of mutations, digested with NdeI/HindIII, and subcloned into the pET29a plasmid, predigested with the same restriction enzymes. The expression plasmid was then transformed into BL21 cells.

Expression, Refolding, and Purification of LBD—BL21 cells (500 ml) were grown in a 2.5-liter flask in Terrific Broth (TB) medium at 37° C. to an $A_{600}$ of 0.9, and IPTG was then added to a final concentration of 1 mM. Cells were grown for an additional 4 h and then harvested by centrifugation at 16,000×g for 10 min and frozen. The bacterial pellet from 3 liters of culture was thawed on ice and resuspended in lysis buffer (10 mM Tris-HCl, 10 mM EDTA, pH 8) containing 0.5 mg lysozyme/ml. Inclusion bodies were then prepared as described previously and frozen (Gertler, A. et al. (1998) *FEBS Lett.* 442, 137-140). Subsequently, inclusion bodies obtained from 3 liters of bacterial culture were solubilized in 600 ml of 4.5 M urea, pH 11.5, in the presence of 10 mM cysteine. After 1 h of stirring at 4° C., the solution was diluted with 2 vol of 0.75 M L-Arg to a final concentration of 0.5 M and stirred for an additional 10 min, and then the clear solution was dialyzed against 5×10 liters of 10 mM Tris-HCl, pH 9. The protein was then applied to a Q-Sepharose column (2.5×6 cm) pre-equilibrated with 10 mM Tris-HCl, pH 9. The breakthrough fraction (which contained no LBD) was discarded, the absorbed protein was eluted in a stepwise manner by increasing concentrations of NaCl in the same buffer, and 5-ml fractions were collected. Protein concentration was determined by absorbance at 280 nm.

Determination of the Amino-terminal Sequence—Automated Edman degradation technique was used to determine the amino-terminal protein sequence. Degradation was performed on an ABI Model 470A gas-phase sequencer (Foster City, Calif.) using the standard sequencing cycle. The respective phenylthiohydantoin derivatives were identified by reverse phase-high pressure liquid chromatography analysis, using an ABI Model 120A phenylthiohydantoin analyzer fitted with a Brownlee 2.1-mm inner diameter phenylthiohydantoin-$C_{18}$ column.

Determination of Purity and Monomer Content—SDS-PAGE was carried out according to Laemmli (Laemmli, U. K. (1970) *Nature* 227, 680-685) in a 15% polyacrylamide gel under reducing and non-reducing conditions. Gels were stained with Coomassie Brilliant Blue R. Gel filtration chromatography was performed on a Superdex™75 HR 10/30 column with 0.2-ml aliquots of the Q-Sepharose column-eluted fractions using 25 mM TN buffer (Tris-HCl buffer, pH 8, containing 150 mM NaCl). Freeze-dried samples were dissolved in $H_2O$.

Determination of CD Spectra and Extinction Coefficients—The CD spectra in millidegrees were measured with an AVIV model 62A DS circular dichroism spectrometer (Lakewood, N.J.) using a 0.020-cm rectangular QS Hellma cuvette. The spectrometer was calibrated with camphorsulfonic acid. The absorption spectra were measured with an AVIV model 17DS UV-visible IR spectrophotometer using a 1.000-cm QS cuvette and correction for light scattering. Lyophilized protein was dissolved in water, dialyzed against 50 mM phosphate buffer, pH 7.5, for 20 h, and then centrifuged at 11,000×g for 10 min. The CD measurements were performed at 25.0° C. as controlled by thermoelectric Peltier elements to an accuracy of 0.1° C. The CD spectra were measured in five repetitions resulting in an average spectrum for each protein. Standard deviation of the average CD signal at 222 nm was in the 5% range. For the secondary structure determination, the CD data were expressed in degree $cm^2$/dmol per mean residue, based on a molecular mass of 24.6 kDa calculated for the protein from the 208 amino acids. The protein concentration was determined by the Biuret method (Goa, J. (1953) *Scand. J. Clin. Lab. Invest.* 5, 218-222) in five repetitions at different dilutions for each protein, using lysozyme as a reference ($A_{280}$=0.388 at 1 mg/ml) (Pace, C. N. et al (1995) *Protein Sci.* 4, 2411-2423). The obtained protein concentration values were applied for both extinction coefficient determination at 280 nm and for secondary structure determinations using CD spectra. The secondary structure of the protein was calculated by applying the procedure and computer program CONTIN developed by Provencher and Glöckner (Provencher, S. W. et al (1981) *Biochemistry* 20, 33-37). The program determines a-helices, β-strands, and β-turns as percentage of amino acid residues involved in these ordered forms. Unordered conformation was determined as unity minus the sum of all elements of the secondary structure (Venyaminov, S. Y. et al (1996) in *Circular Dichroism and the Conformational Analysis of Biomolecules* (Fasman, G. D., ed), pp. 69-107, Plenum Publishing Corp., New York). In the present study, for calculations by the CONTIN program, a set of standard CD spectra of 17 proteins (Sreerama, S. et al (1993) *Anal. Biochem.* 209, 3244) was employed.

Induction of *Escherichia coli* cells by IPTG led to the appearance of a weak band corresponding to LBD, which appeared as a main band in the inclusion bodies (see FIG. 1, lanes 2 and 3). Inclusion bodies collected from IPTG-induced cells were solubilized and refolded as described under "Experimental Procedures." Subsequently, the LBD protein was purified by one-step ion-exchange chromatography on a Q-Sepharose column. Every fifth fraction was tested for LBD appearance by gel filtration on a Superdex™75 HR column. Three fractions containing LBD protein, eluted, respectively, with 100, 125, and 150 mM NaCl from the Q-Sepharose column, were collected and pooled (underlined in FIG. 2). Each of those pools was analyzed by gel filtration on a Superdex™75 HR column. Only the fraction eluted with 100 mM contained over 95% monomeric protein and 5% dimers, whereas fractions eluted with higher NaCl concentrations contained higher amounts of dimmers and oligomers. These results were also verified by SDS-PAGE, showing that only the first fraction contained monomeric LBD under both reducing and non-reducing conditions (FIG. 1, lanes 4 and 8) with an approximate molecular mass of 25 kDa, close to the predicted value of 24,616 Da, calculated for Met-LBD. Pools eluted at 125 and 150 mM contained a mixture of monomers and dimers, the latter formed by S—S links (see FIG. 2, lanes 5 and 6 versus lanes 9 and 10). The yield of the monomeric fraction (100 mM NaCl eluate) was 4 mg from 3 liters of bacterial culture. The amino-terminal sequence of the purified LBD was (Met)-Ala-Ile-Asp-Val-Asn-Ile-Asn-Ile-Ser-Xaa-Glu (SEQ ID NO:5), as predicted from the primary structure (Haniu, M. et al. (1998) *J. Biol. Chem.* 273, 28691-28699), with an additional Met residue. The unidentified amino acid at position 10 is most likely Cys, which could not be identified by the present method. The results of the CD analysis are presented in FIG. 3. The secondary structure calculations revealed the contents of a-helices, β-strands, β-turns, and unordered forms to be (mean±S.D.) 6.6±0.4, 37±1.2, 25±1.0, and 31±1.6%, respectively, indicating strong similarity to the structure observed in the ECDs of hGH, human prolactin, and rat prolactin receptors (De Vos, A. M. et al (1992) *Science* 255, 306-312; Somers, W. et al (1994) *Nature* 372, 478481; Elkins, P. A. et al (2000) *Nat. Struct. Biol.* 7, 808-815). The specific absorbance of the protein (1 mg/ml at $A_{280}$) was 1.95, calculated according to Perkins (Perkins, S. J. (1986) *Eur. J. Biochem.* 157, 169-180), and this value was used in the calculations in other experiments. LBD lyophilized in the presence of excess $NaHCO_3$ retained its monomeric form, and after solubilization (at 0.5 mg/ml), no dimerization or oligomerization was observed in a solution kept at 4° C. for several days.

EXAMPLE 2

Determination of Complex Stoichiometry

Complexes between LBD and hLEP were prepared at various molar ratios in TN buffer. After a 20- to 30-min incubation at room temperature, 200-μl aliquots were applied to a Superdex™75 HR 10/30 column. To determine the molecular mass of the complex, the column was calibrated with several pure proteins.

Binding Assays—Radiolabeled human $^{125}$I-leptin served as a ligand, and other (human, ovine, and chicken) nonlabeled leptins served as competitors. The experiments were conducted using either recombinant LBD or homogenates of BAF/3 cells stably transfected with the long form of hLEP receptor. In the latter case, the cells were cultured in Dulbecco's modified Eagle's medium supplemented with 5% fetal calf serum in the presence of IL-3 to minimize leptin-receptor down-regulation until a concentration of $10^6$ cells/ml was reached. Then the cells were spun and stored at −70° C. Prior to each experiment, the cells were thawed, suspended at $10^6$ cells/150 μl of reaction buffer (12.5 mM sodium barbiturate, pH 8.6, buffer containing 0.1% (w/v) bovine serum albumin, 7.5 mM EDTA, 150 mM NaCl, and 0.1% (w/v) Triton X-100), and homogenized with a Polytron for 30 s at 10,000 rpm on ice. Each tube contained 150 or 200 μl of reaction buffer in the case of the assay with the cells or recombinant LBD, respectively, 100 μl of $^{125}$I-hLEP (100,000 cpm for cells or 180,000 cpm for binding domain assays), and 100 μl of different leptin solutions (providing 0-5000 ng/tube) in the reaction buffer, and the reaction was started by addition of 150 μl of cell homogenate or 100 μl of LBD (20 ng). The tubes were incubated for 24 h at room temperature. Then the leptin receptor complex was precipitated by adding 250 μl of 1% (w/v) bovine immunoglobulin and 500 μl of 20% (w/v) polyethylene glycol. After thorough mixing, the tubes were incubated for 20 min at 4° C. and centrifuged at 12,000×g for 15 min at 4° C. Then supernatant was carefully aspirated, and the precipitates were counted in a Kontron ?-counter. Human leptin was iodinated according to a protocol described previously for the iodination of human growth hormone (hGH) (Gertler, A. et al (1984) *Mol. Cell. Endocrinol.* 34, 51-57).

Kinetic Measurements of LBD-hLEP Interactions—All experiments were performed at 25° C. using surface plasmon resonance (SPR) methodology. The kinetics and equilibrium constants for the interaction between hLEP and LBD were determined using the Biacore 3000 system (Uppsala, Sweden). hLEP was immobilized in a flow cell of a research-grade CM5 sensor chip using amine-coupling chemistry (Lofas, S. et al (1990) *J. Chem. Soc. Chem. Commun.* 21, 1526-1528). The immobilization steps were carried out at a flow rate of 10 μl/min in HBS-EP buffer. The surface was activated for 7 min with a mixture of N-hydroxysuccinimide (0.05 M) and N-ethyl-N'(3-dimethylaminopropyl)-carbodiimide hydrochloride (0.2 M). hLEP was injected at a concentration of 50 μg/ml in 10 mM acetate, pH 3.5, until the desired level (1000 resonance units) was achieved. Ethanolamine (1 M, pH 8.5) was injected for 7 min to block the remaining activated groups. A control surface was prepared by activating the carboxyl groups and then blocking the activated groups by ethanolamine as described. For the binding studies, the LBD, resuspended in HBS-EP buffer, was passed at different concentrations (31.25, 62.5, 125, and 250 nM) through both flow cells at a rate of 30 μl/min. Regeneration of the surface after each interaction was performed by using a 10-μl pulse of 10 mM glycine buffer, pH 2. The experiment was done using the kinetics Wizard of the Biacore control software, which corrects automatically for refractive index changes and nonspecific binding by subtraction of the responses obtained for the control surface from the data obtained for the interaction with hLEP. The obtained binding curves were fitted to the association and dissociation phases at all leptin receptor concentrations simultaneously using evaluation software from Biacore. The best fit was obtained for a simple bimolecular interaction (Langmuir model).

Figure 4:
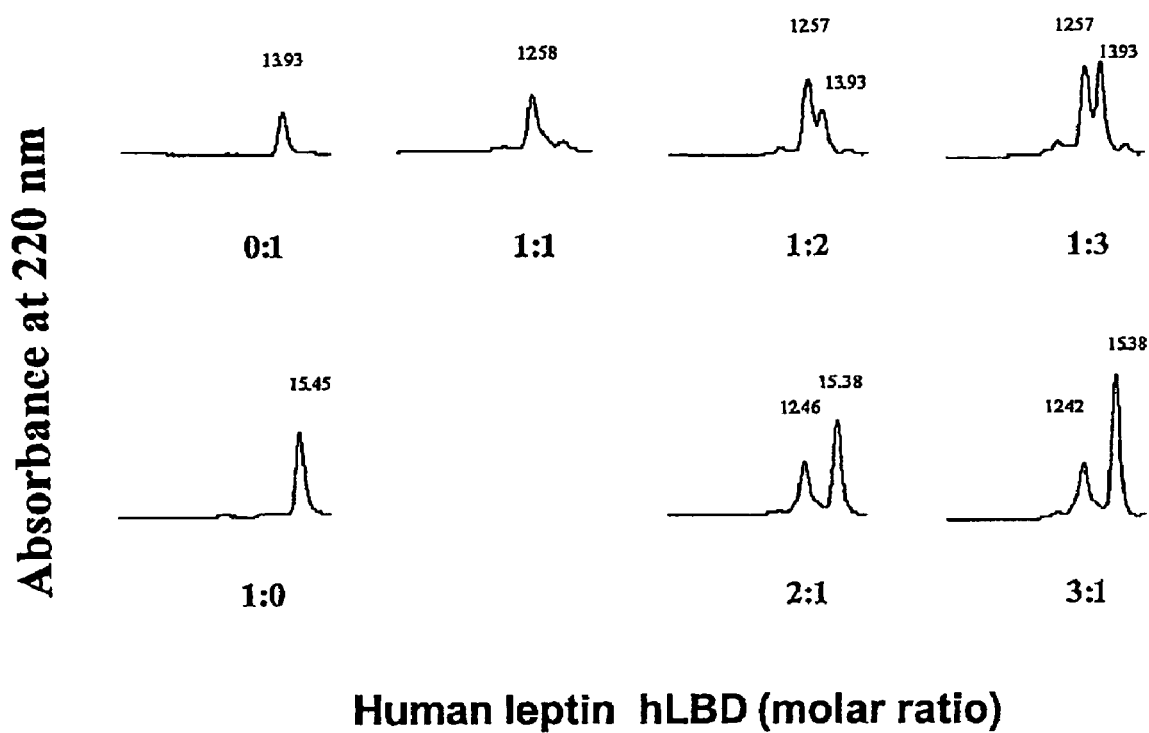
FIG. 4 illustrates a gel filtration of complexes of hLEP and on a Superdex™75 HR 10/30 column. Complex formation was carried out during a 20- to 30-min incubation at room temperature in TN buffer using various hLEP:LBD molar ratios and then aliquots (200 µl) of the incubation mixture were applied to the column, pre-equilibrated with the same buffer. The initial hormone concentration (2 µM) was constant in all cases in the upper row, whereas in the lower row the LBD concentration was held constant (4 µM). The column was developed at 0.8 ml/min and calibrated with bovine serum albumin (66 kDa, RT=10.78 min), egg albumin (45 kDa, RT=12.11 min), extracellular domain of hGH receptor (28 kDa, RT=13.52 min), and ovine placental lactogen (23 kDa, RT=14.12 min). Protein concentration in the eluate was monitored by absorbance at 220 nm. Each experiment was conducted at least three times.

Detection of LBD-hLEP Complex by Gel Filtration—The experiment was performed using either a constant concentration of hLEP and increasing concentrations of LBD or vice versa. As shown in FIG. 4, both components added alone were eluted from the column as monomers at the respective RTs of 15.45 and 13.93 min. Their molecular masses calculated from the standard curve were 15.3 and 24.8 kDa, respectively, close to the predicted theoretical values. Mixing the two components in a 1:1 molar ratio resulted in a new single peak with an RT corresponding to molecular mass of 39.9 kDa, indicating 1:1 complex formation. Changing the molar ratio by adding excess hLEP or LBD did not change the RT of this peak, further proving that under the present experimental conditions, formation of LBD·hLEP complexes at a 2:1 molar ratio cannot be detected.

Binding Experiments—To evaluate whether the binding properties of LBD are similar to those of the full-size membrane-embedded leptin receptor, the binding of radio-iodinated hLEP was compared to the purified LBD and to a homogenate of BAF/3 cells stably transfected with the long form of human leptin receptor. In addition to hLEP, ovine and chicken leptins were also employed to displace the radioactive ligand. Results shown in FIG. 5 highlight two differences: (i) the $K_d$ for binding of hLEP to LBD was 7-fold higher than to the BAF/3 homogenate (5.91±1.10 versus 0.83±0.14 nM, mean±S.E.), and (ii) chicken leptin could displace binding of help to BAF/3 homogenate (though its capacity was ~20-fold lower than that of hLEP) but not to LBD. In contrast, the differences between human and ovine leptins were minimal.

Figure 6:
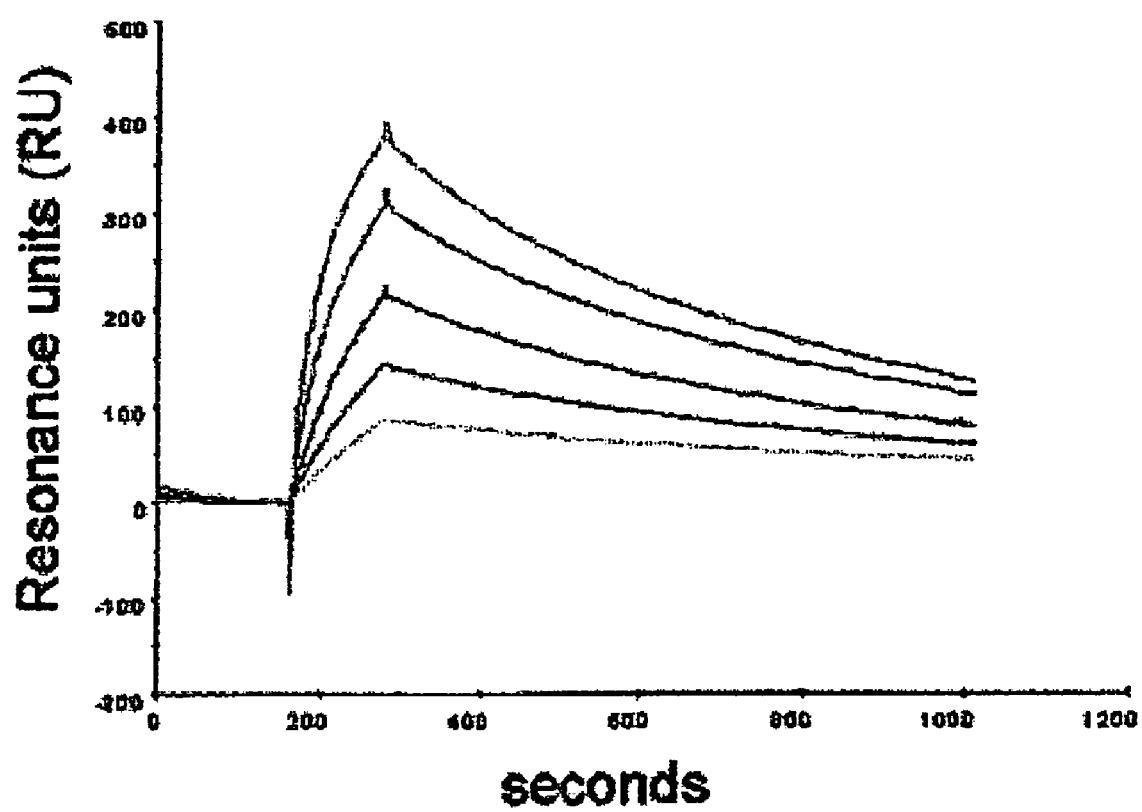
FIG. 6 illustrates an association and dissociation kinetics between LBD and hLEP linked covalently to carboxymethylated dextran through amino groups.

SPR Determination of the Interaction between hLEP and LBD—The interactions of hLEP and LBD were analyzed by comparison with a theoretical model using Chi-square analysis. In all cases, the interactions proved to be best suited to the 1:1 model. Analysis of the data presented in FIG. 6 resulted in a $k_{off}$ constant (mean±S.E.) of $1.85\pm0.30\times10^{-3}$ s$^{-1}$, indicating a complex half-life of 6.24 min. The $k_{on}$ calculated by averaging the results obtained at five concentrations of LBD was $1.2\pm0.30\times10^{5}$ mol$^{-1}$ s$^{-1}$ and the corresponding $K_d$ value was calculated as $1.54\times10^{-8}$ M.

EXAMPLE 3

Proliferation Assay

BAF/3 Proliferation Assay—The proliferation rate of leptin-sensitive BAF/3 1442-CI4 cells stably transfected with the long form of human leptin receptor was used to estimate self- and antagonistic activity of recombinant LBD, using the thiazolyl blue method as described (Raver, N. et al (2000) *Protein Expression Purif.* 19, 30-040). To determine antagonistic activity of LBD, human, ovine, or chicken leptin were added to each well (to a final concentration of 0.57 nM) with various concentrations of recombinant LBD. The average absorbance in wells with wild-type leptins after subtraction of the negative control was used as a positive control to calculate percent inhibition caused by LBD.

Figure 7:
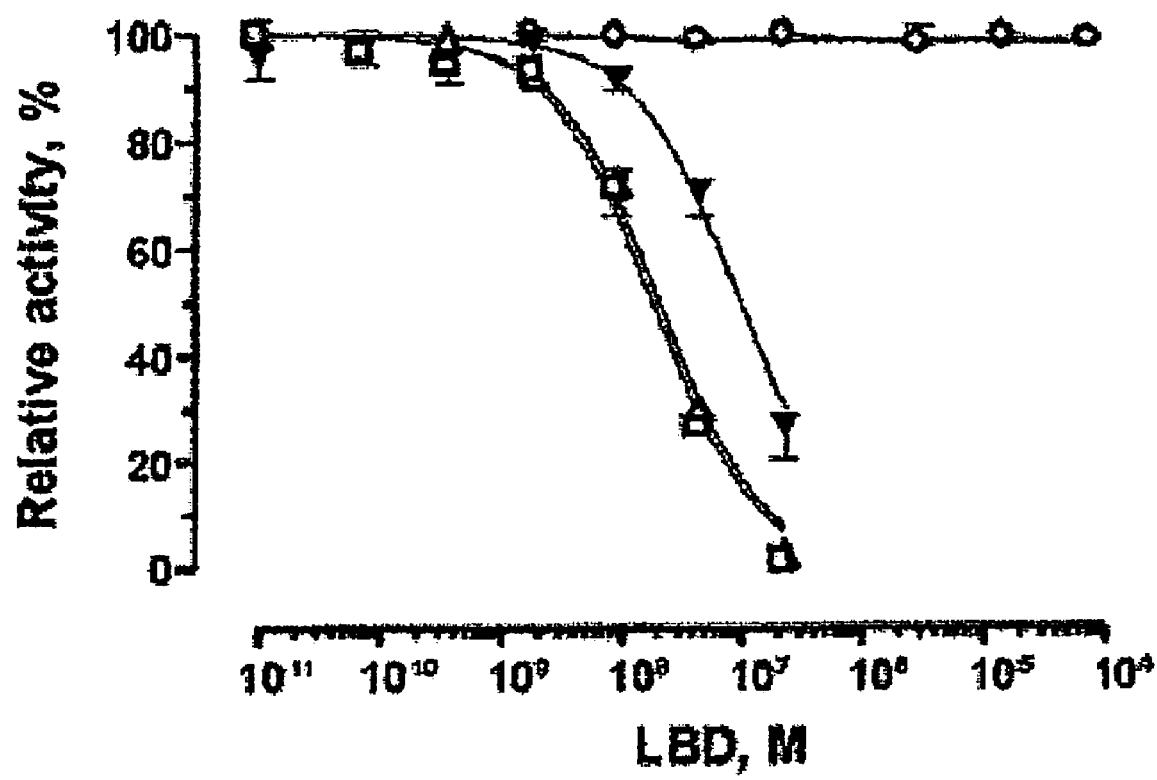
FIG. 7 illustrates an inhibition of human (□)-, ovine (Δ)-, chicken (▼)-, and interleukin-3 (○)-stimulated proliferation of BAF/3 cells transfected with the long form of human leptin receptor. Synchronized cells were grown for 48 h in the presence of human, ovine, or chicken leptin (0.57 nM) or interleukin-3 (6 nM) and various concentrations of LBD. The number of cells was determined subsequently by the thiazolyl blue method (see text). Full lines and $IC_{50}$ values were calculated using the PRIZMA curve-fitting program (Author, A. (1994) *GraphPad Prism™*, Version 2.0, GraphPad Software Inc., San Diego, Calif.).

Inhibition of Human, Ovine, and Chicken Leptin-induced Proliferation of BAF/3 Cells by LBD—BAF/3 cells stably transfected with the long form of human leptin receptor (Verploegen, S. A. B. W. et al (1997) *FEBS Lett.* 405, 237-240) were chosen to test this activity, because proliferation of those cells can be stimulated by both leptin from various sources (Gertler, A. et al. (1998) *FEBS Lett.* 442, 137-140; Raver, N. et al (1998) *Protein Expression Purif* 14, 403-408; Raver, N. et al (2000) *Protein Expression Purif* 19, 30-40) and by IL-3 (Verploegen, S. A. B. W. et al (1997) *FEBS Lett.* 405, 237-240) and by IL-3. LBD inhibited the proliferation of BAF/3 cells stimulated, respectively, by human, ovine, and chicken leptins in a dose-dependent pattern, but the molar excess required to achieve 50% inhibition in cells stimulated by human, ovine, or chicken leptins was rather large, namely 200, 200, and 600 molar excess, respectively (FIG. 7). The inhibitory effect was, however, very specific, as no inhibition was observed in cells stimulated by IL-3 even at a $10^5$ molar excess of LBD.

In summary, human LBD in low concentrations (nM) blocked leptin induced, but not interleukin-3-induced proliferation of BAF/3 cells stably transfected with the long form of human leptin receptor, in dose dependent manner, while in high concentrations of LBDs, they were able to induce proliferation by themselves.

EXAMPLE 4

Comparison of Kd Values for Interaction of Human Leptin with Human Leptin Receptors The results herein demonstrate production of recombinant LBD, a 208-amino acid fragment of the ECD of human leptin receptor (corresponding to residues 428 to 635 of the full-size WT receptor), which has the ability to bind human and other leptins. A scale-up of its production will enable an increase in yield and the production of material for both structural and in vivo studies. The electrophoretically pure monomeric protein was capable of forming a stable 1:1 complex with hLEP. The present studies answer the two questions regarding whether LBD binds leptin at an affinity similar to that of the full-size leptin receptor ECD, and whether the affinities of the soluble and membrane-embedded leptin receptors are comparable. Several binding experiments using either classical methods or SPR with pure recombinant LBD and membrane-embedded leptin receptor in BAF/3 cells stably transfected with this protein were performed. The results are compiled in Table 1 and compared with results reported by others.

TABLE 1

Comparison of Kd values for interaction of human leptin with human leptin receptors

| Leptin receptor | $K_d$ or $IC_{50}$ nM | Method | Reference |
|---|---|---|---|
| WT in BAF/3 cell homogenate | 0.83 | Binding | Present examples |
| WT in BAF/3 cell homogenate | 1.03[a] | Binding | Present examples |
| LBD | 5.93 | Binding | Present examples |
| LBD | 15.3 | SPR | Present examples |
| LBD | 7.6[a] | Binding | Present examples |

TABLE 1-continued

Comparison of Kd values for interaction of human leptin with human leptin receptors

| Leptin receptor | $K_d$ or $IC_{50}$ nM | Method | Reference |
|---|---|---|---|
| WT in COS cells | 0.6[a] | Binding | Fong, T. M. et al (1998) Mol. Pharmacol. 53, 234-240 |
| Minimal BD in COS cells[b] | 1.3[a] | Binding | Fong, T. M. et al (1998) Mol. Pharmacol. 53, 234-240 |
| WT in COS7 cells | ~0.2[a] | Binding | Liu, C. et al (1997) Endocrinology 138, 3548-3554 |
| ECD secreted by COS7 cells[c] | ~0.2[a] | Binding | Liu, C. et al (1997) Endocrinology 138, 3548-3554 |
| WT COS7 cells | 0.9 | Binding | Luoh, S. M. et al (1997) J. Mol. Endocrinol. 18, 77-85 |
| ECD secreted by Sf9 cells[d] | 9.5 | SPR | Rock, F. L. et al (1996) Horm. Metab. Res. 28, 748-750 |
| ECD in human serum | 0.42 | Binding | Wu, Z. et al (2002) J. Clin. Endocrinol. Metab. 87, 2931-2939 |

[a]IC50 values.
[b]The minimal binding domain (BD) consisting of leptin BD (LBD) with upstream immunoglobulin domain anchored in COS cells.
[c]Full-size extracellular domain (ECD) engineered to be secreted.
[d]Partially purified His6 and FLAG-tagged ECD prepared in Sf9 cells using baculovirus expression system.

To answer the first question, comparison of the binding of LBD to full-size leptin receptor ECD (Rock, F. L. et al (1996) Horm. Metab. Res. 28, 748-750) is readily made, because both studies were conducted by a similar method, SPR. This comparison shows that the affinities are quite similar (15.3 versus 9.5 nM) and suggests that other parts of the ECD beyond the LBD region play only a minor, if any, role in binding of the hormone. This conclusion is also supported by others (Fong, T. M. et al (1998) Mol. Pharmacol. 53, 234-240) who have shown a rather minor difference (0.6 versus 1.3 nM) in the affinity of the WT receptor as compared with the minimal binding domain that consists of the LBD region flanked by the upstream 100-amino acid long immunoglobulin domain. In contrast, other data (Liu, C. et al. (1997) Endocrinology 138, 3548-3554) are not consistent with this conclusion, as the $IC_{50}$ for LBD is 38-fold higher than that of the full-size ECD. However, this comparison should be made with caution, because the methodology applied during the precipitation step in the binding experiments, in particular in those studying the interaction of soluble proteins, may affect the experimental results. Most of the results also suggested that the affinity of the membrane-embedded receptors is higher than that of the soluble domain. This is similar to an analogous situation existing with several prolactin receptors (Sandowski, Y. et al (1995) Mol. Cell. Endocrinol. 115, 1-11; Tchelet, A. et al (1995) J. Endocrinol. 144, 393-403; Sandowski, Y. et al (2000) Gen. Comp. Endocrinol. 118, 302-309), with the exception of rabbit prolactin receptor ECD (Bignon, C. et al (1994) J. Biol. Chem. 269, 3318-3324). Again, this conclusion has to be approached with caution, because as already stated, the methodology applied during the precipitation step may affect the results.

To better understand the LBD-hLEP interaction, a model of the 1:1 complex based on the known three-dimensional x-ray structures of the cytokine-binding region of gp-130 and the hGH receptor-ECD (PDB accession codes IBQU and 1AXI, respectively) was built. Based on the sequence alignments of these proteins with that of LBD, amino acid mutations, insertions, and deletions were applied by using the graphic program O (Jones, T. A. et al (1991) Acta Crystallogr. Sect. A 47, 110-119). The modeled LBD structure and the known three-dimensional structure of hLEP (PDB accession code 1AX8 (Zhang, F. et al (1997) Nature 387, 206-209) were used to construct the 1:1 LBD·hLEP complex. The 1:1 model was then minimized via CNS software (Brünger, A. T. et al (1998) Acta Crystallogr. Sect. D Biol. Crystallogr. 54, 905-921). The resulting model was then utilized to assess plausible amino acid residues that may either enhance or reduce binding to the leptin hormone, and the final model is presented in FIG. 8.

Figure 8:
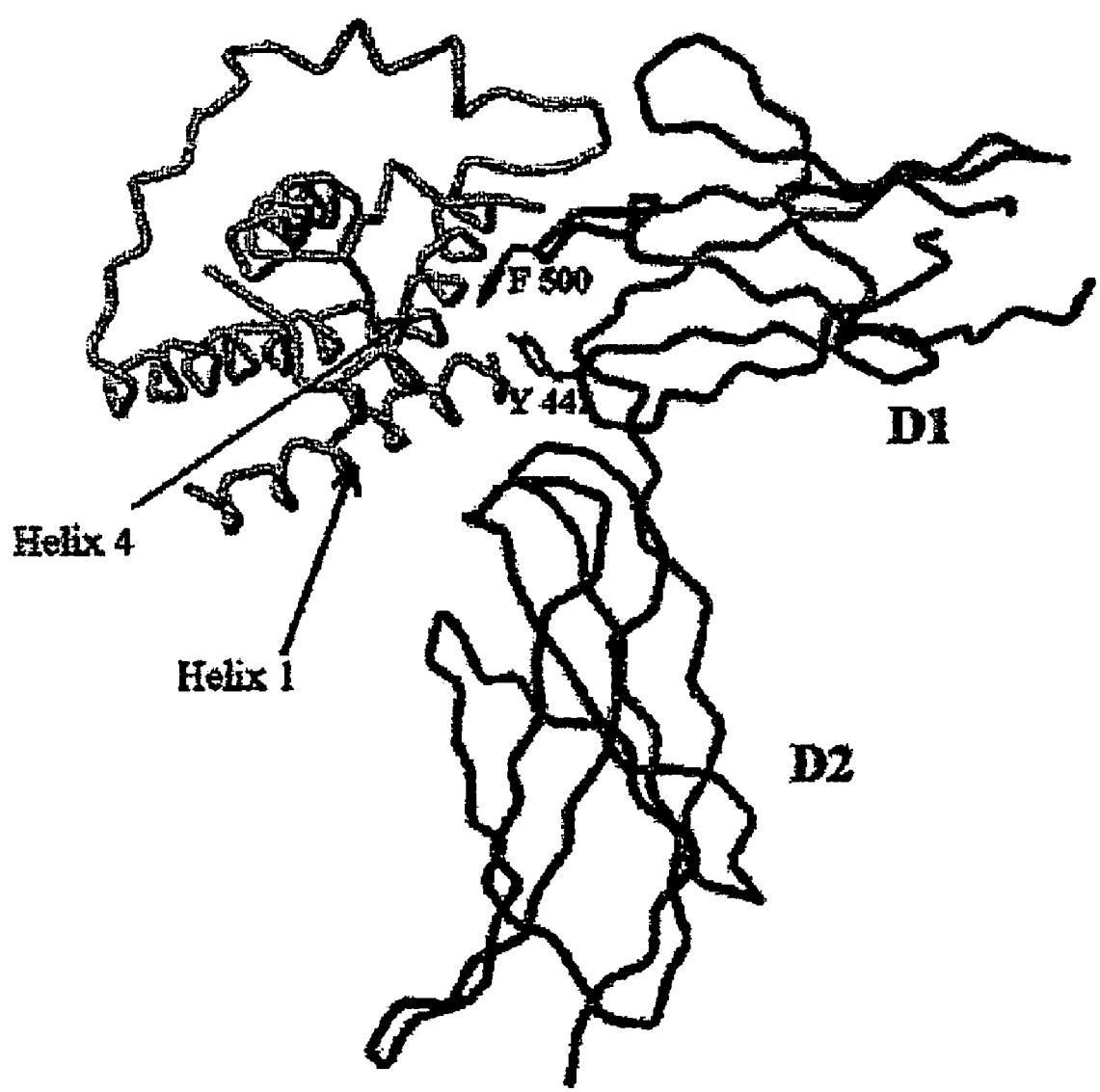
FIG. 8 illustrates a schematic representation of the human leptin-LBD 1:1 complex. The amino- and carboxyl-terminal domains of LBD are denoted as D1 and D2, respectively. Tyr-441 and Phe-500, which may be crucial for leptin binding, are labeled and shown in red.

The ligand-binding determinants of cytokine receptor ECDs consist of six segments denoted L1-L6 (De Vos, A. M. et al (1992) Science 255, 306-312; Livnah, O. et al (1996) Science 273, 464-471). These segments are positioned in three loop regions, L1-L3 situated in the amino-terminal domain, L4 in the interdomain linker, and L5 and L6 in two main loops, located in the carboxyl-terminal domain. Previous structural and mutational research with the hGH and hGH receptor ECD system has indicated that the binding epitope consists of many interacting residues, some of which are crucial for ligand binding (Clackson, T. et al (1995) Science 267, 383-386). One of these residues is Phe-500, located in loop L3, where an aromatic residue is conserved throughout the sequences of the cytokine receptor superfamily. An additional residue that may have an impact on leptin binding is Tyr-441, located in L1 (FIG. 8). Results obtained by the present inventors indicate that mutation of Phe to Ala abolished leptin binding capacity and mutation of Tyr to Ala reduced leptin binding capacity. The WS motif consisting of residues WSXaaWS (622-626) (SEQ ID NO:6) in the LBD, and regarded as a signature sequence of the cytokine receptor superfamily (Baumgartner, J. W. et al (1994) J. Biol. Chem. 269, 29094-29101), is located toward the last strand (β-G) of the carboxyl-terminal domain (D2). An additional Trp (Trp-583) extends the WS motif into the LBD. Two arginine residues (Arg-612 and Arg-573) are sandwiched between each tryptophan pair to form an extended p-cation system.

Although the affinity of LBD toward hLEP is somewhat lower than that of the full-length, membrane-embedded receptor-soluble system could be useful as a model for mapping of the binding epitope of both receptor and hormone. A short fragment of the receptor with high affinity binding capabilities to the hormone provides a higher potential system for crystallization and subsequent structural studies. Furthermore, extensive mutagenesis and subsequent binding assays would identify the crucial amino acid residues in the binding sites and may provide a platform for the design of small molecules and/or peptidic high affinity binders of leptin receptor.

EXAMPLE 5

Chicken Leptin Binding Domain (chLBD)

The present inventors have prepared LBD from chicken receptor from DNA provided by Dr. Miri Einat (Agricultural Research Organization, the Volcani Center, P.O. Box 6, 50250 Beit Dagan, Israel) and characterized binding and functional properties thereof. Such properties were compared between the recombinant human (amino acids 428 to 635) and chicken (amino acids 419 to 624) leptin receptor-binding domains (LBD). Primers used for cloning the chicken receptor binding domain were designed based on the sequence of the human receptor binding domain and the known sequence of the complete chicken receptor gene. The amino acid sequence of the chicken leptin receptor binding domain is provided at SEQ ID NO:8 and the nucleotide sequence that encodes the chLBD is provided at SEQ ID NO:7. The LBDs were subcloned, expressed in prokaryotic host, refolded and purified as at least 95% monomers, revealed by SDS-PAGE and gel filtration under non denaturative conditions. Ten to twenty milligram preparations of the chicken lepin receptor binding domain are readily prepared.

Both LBDs were able to bind human, ovine and chicken leptins (the latter produced according to the sequence published by Taouis et al. Gene 1998 Feb. 27; 208(2):239-42) and formed with all of them stable 1:1 complexes. The binding kinetic constants for the complex formation with human and ovine leptins were measured by surface plasmon resonance methodology with the strongest interaction occurring between hLBD and hLeptin and the weakest interaction between chLBD and chLeptin as shown in Table 2.

TABLE 2

The kinetic constants measured by surface plasmon resonance for complex formation of human and chicken leptin-binding domains (LBD) with either human or chicken leptin.

| LBD | Ligand | $k_{on}^a$, $mol^{-1}s^{-1}$ | $k_{off}^a$, $s^{-1}$ | $K_d^a$, mol |
|---|---|---|---|---|
| Human | Human leptin | $1.20 \pm 0.23 \times 10^5$ | $1.85 \pm 0.30 \times 10^{-3}$ | $1.54 \times 10^{-8}$ |
|  | Chicken leptin | $1.35 \times 10^4$ | $5.20 \times 10^{-3}$ | $3.80 \times 10^{-7}$ |
| Chicken | Human leptin | $1.83 \pm 0.95 \times 10^5$ | $1.43 \pm 0.34 \times 10^{-2}$ | $7.85 \times 10^{-8}$ |
|  | Chicken leptin | $5.83 \pm 1.53 \times 10^4$ | $7.60 \pm 1.2 \times 10^{-2}$ | $1.30 \times 10^{-6}$ |

$^a$—mean ± S.E.

The data clearly show the ability of chicken leptin receptor binding domain to bind to human leptin.

Figure 5:
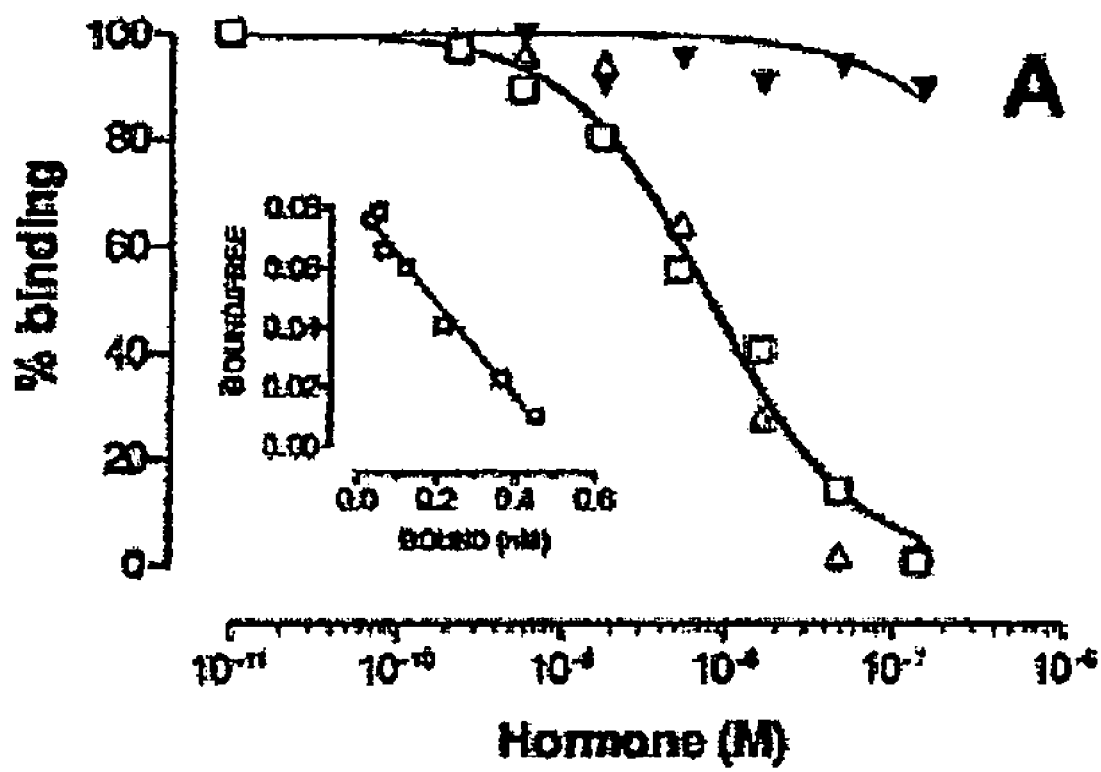
FIG. 5 illustrates a competition of unlabeled human leptin (□), ovine leptin (Δ), and chicken leptin (▼) with $^{125}$I-human leptin (80,000 cpm/tube) for binding to LBD (A) and to homogenate of BAF/3 cells (B). The specific binding (%) in experiments performed with human, ovine, and chicken leptins and their mutants were, respectively, 7.3% in A, and 8.1% in B, and the nonspecific binding was respectively, 5.4 and 14%. All values for specific binding were normalized, and the solid lines and the $IC_{50}$ values were calculated using the PRIZMA curve-fitting program (Author, A. (1994) *GraphPad Prism™*, Version 2.0, GraphPad Software Inc., San Diego, Calif.).
Figure 5:
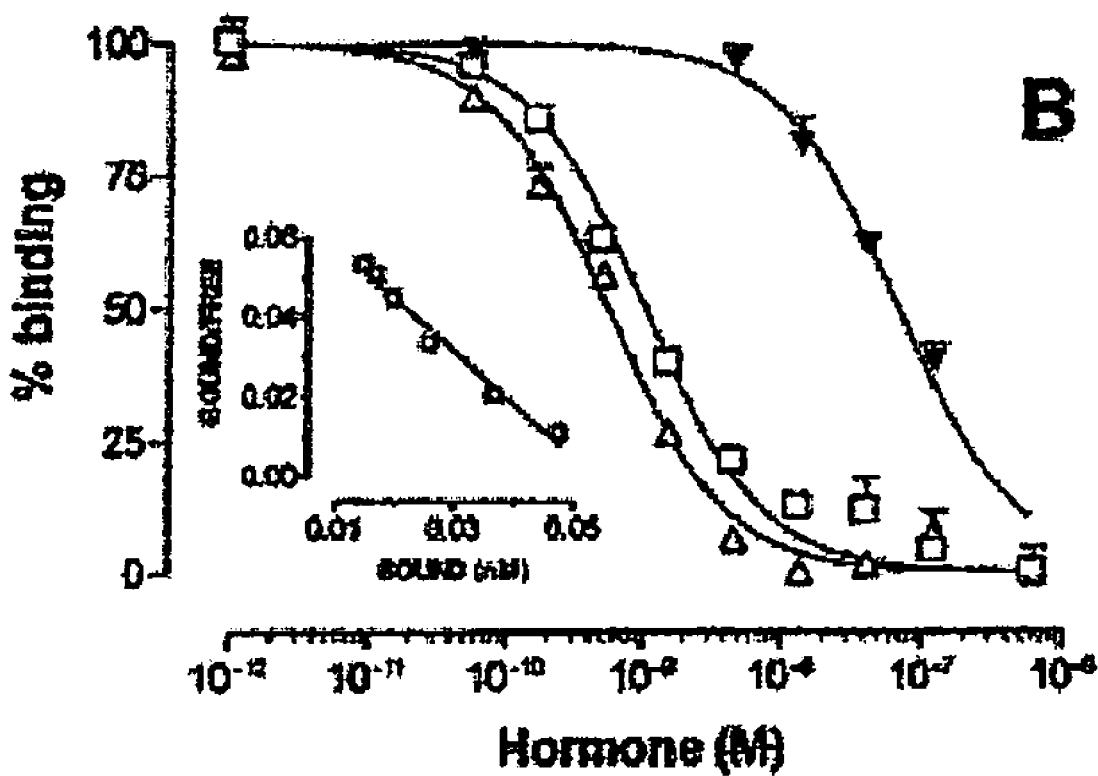
Figure 9:
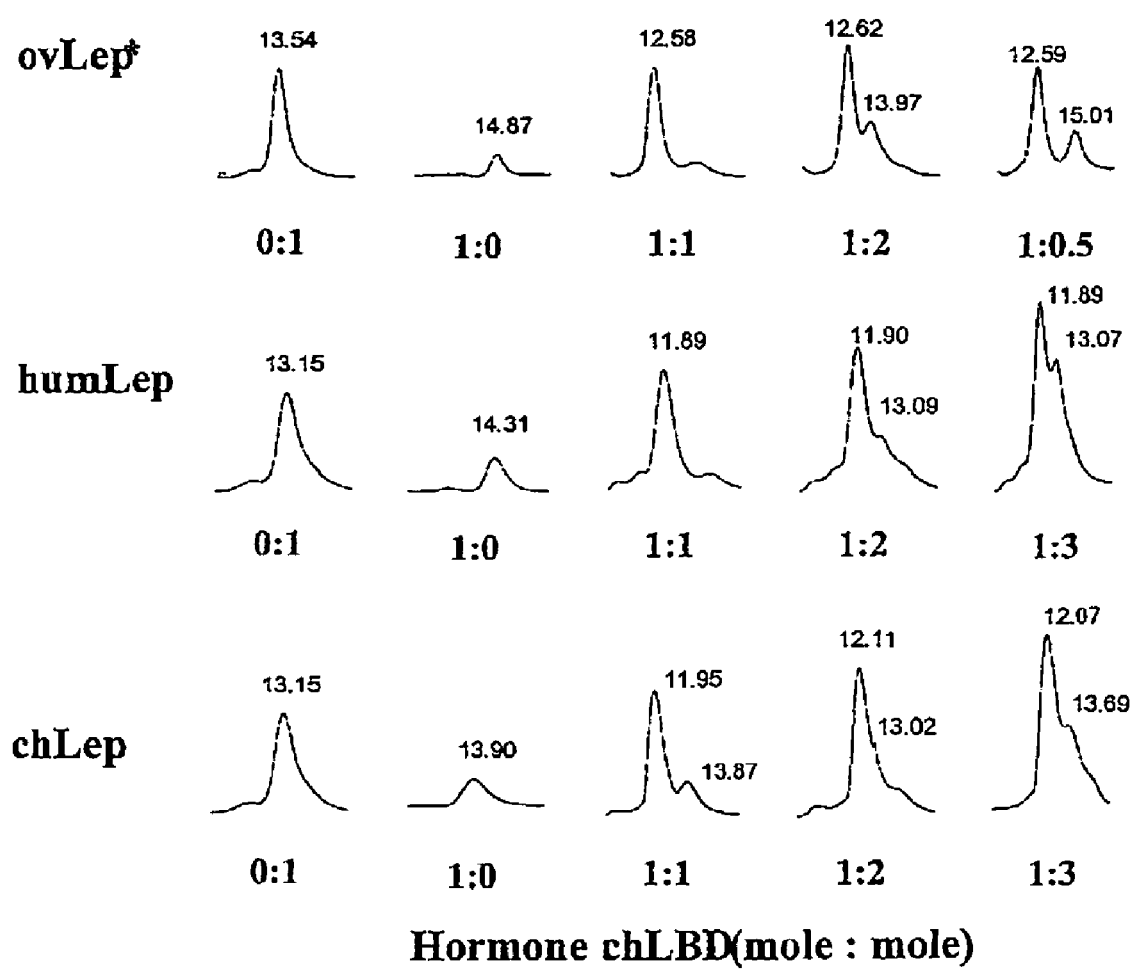
FIG. 9 illustrates gel filtration analysis of complexes at various molar ratios between ovine, human and chicken leptins and chLBD. The calculated MW of the chLBD in all experiments was the same.
Figure 10:
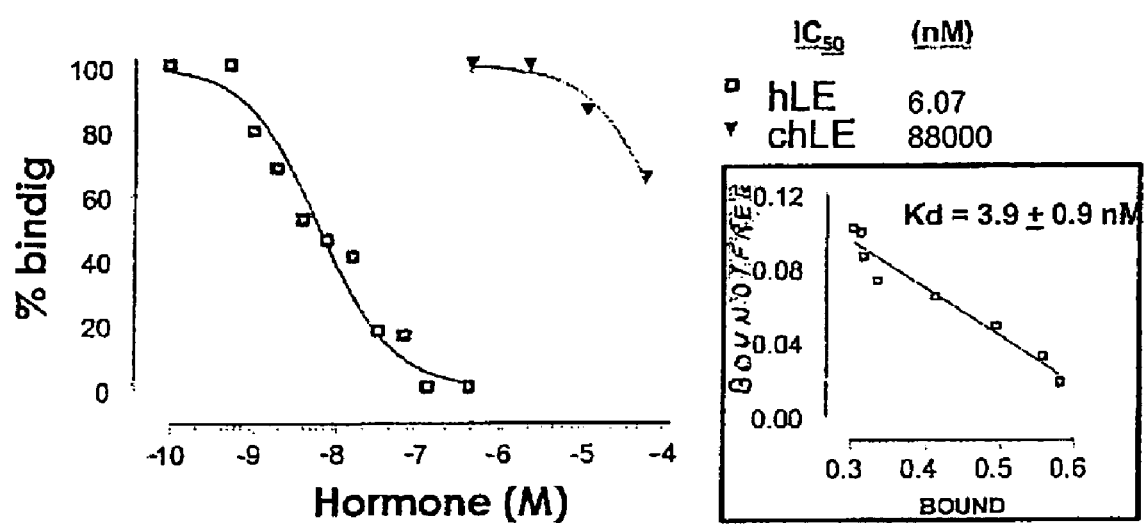
FIG. 10 illustrates inhibition of binding of 125I-hLep to chLBD by ovine, human and chLeptin.

Incubation of LBD with leptin effected a unique single peak with a RT corresponding to a 1:1 complex formation (FIGS. 4 and 9). Altering the LBD-leptin molar ratio with excess LBD or leptin did not alter the RT of the complex. ChLeptin was unable to displace 125I-hLeptin bound to either hLBD or chLBD (FIG. 5 and FIG. 10). The inhibition of BAF/3 cell proliferation by hLBD was the lowest when cells were induced by the chLeptin (FIG. 7). The potency of both the human and ovine leptins employed in these studies was equal whether they were reacted with human or chLBD.

EXAMPLE 6

ChLBD as Solid Phase Ligand in Immunoassay for Free Leptin

Leptin is present in blood and other biological fluids in two molecular forms, one as free leptin and another as bound to its soluble receptor. The soluble receptor is the extracellular domain of leptin receptor, which is cleaved off and circulates in blood, and is often referred to as leptin binding protein. There are also other molecules that are known to bind to leptin, but the soluble receptor is the most abundantly bound molecular component. Commercially available immunoassays of leptin measurements address total leptin that constitute both free and bound, and as such, an assay that could measure exclusively free leptin is sought to monitor free leptin levels under different pathophysiological conditions. Such an assay has an immense value in the measurement of stoichiometric ratios of leptin to its circulating soluble receptor under different physiological conditions.

Current commercial assays fail to adequately answer the issue of free leptin measurements as the ligand used as capture (either an affinity purified antibody or antiserum) is targeted to both free and bound leptin. The chLBD is provided herein as a specific ligand for the solid phase by virtue of its binding (more so to human-leptin as observed in the in vitro experiments using recombinant materials) to detect free leptin in a mixture of free and bound leptin, which is the in vivo condition. Initial experiments are done by using rec-human leptin to establish standard curves.

In a two-site immunoassay, ch-LBD has been coated on a plate at neutral pH, and at high pH; rec-human leptin is added, washed, and a second antibody of human-leptin, labeled with HRPO is added. After wash, the bound leptin is measured colorometrically with HRPO-TMB reaction.

In a competitive immunoassay, ch-LBD is coated on a solid phase, and a mixture of unlabeled and labeled (HRPO or biotin) human-leptin is added. After incubation and washes, the displacement is measured colorometrically (addition of TMB in case of HRPO-labeled-leptin, or streptavidine-HRPO, then TMB in case of biotinylated leptin). Standard curves are obtained with rec-human leptin. Typical test samples are human serum or plasma samples.

EXAMPLE 7

Random Serum Samples

Random serum samples were obtained from the clinical laboratories from Hospitals in Toronto, Ontario, Canada. The samples were residuals from routine clinical test samples and were from an adult population (aged 18-72). Upon collection, blood samples were allowed to clot, separated and, after clinical testing, the residuals were stored at −20° C. and used for these studies within 1 week after collection.

EXAMPLE 8

Materials and Reagents

All materials and reagents were of highest quality obtained as previously described (29, 30). Tetramethylbenzidine (TMB) peroxidase substrate system was from Neogen Corporation, Lexington, Ky. Horseradish peroxidase (HRPO) was purchased form Scripps Laboratories (San Diego, Calif.). Microtitration strips and frames were products of Costar, Cambridge, Mass.

Recombinant human leptin, normal goat serum (NGS), normal equine serum (NES), new born calf serum (NBCS), and commercially available human serum were from Diagnostic Systems Laboratories (Webster, Tex.). All sera were heat inactivated and contained 5 mL/L Proclin 300. The composition of the coating and blocking buffers as well as the wash solution were as described previously (29, 30).

EXAMPLE 9

Chicken Leptin Binding Domain (CLBD)

Recombinant chicken leptin binding protein domain (CLBD) was a product of Diagnostic Systems Laboratories (Webster, Tex.).

EXAMPLE 10

Leptin Antibodies

Four mouse monoclonal antibodies and a goat polyclonal antibody evaluated in this report were produced, characterised and purified by DSL (Webster, Tex.). The monoclonal and polyclonal antibodies have been previously screened for leptin specificity. The method for preparation of monoclonal as well as polyclonal antibodies is now well established [Harlow E. et al., 1988 Antibodies. New York, Cold Spring Harbour Laboratory]. As would be appreciated, the antibodies used in the present invention may be monoclonal or polyclonal in nature. Antibodies may be raised against recombinant human leptin or leptin/leptin-binding protein complex purified from human sera. Polyclonal antibodies could be raised in various species including but not limited to mouse, rat, rabbit, goat, sheep, donkey, horse, using standard immunization and bleeding procedures. Animal bleeds with high titres may be fractionated by routine selective salt-out procedures such as precipitation with ammonium sulfate and specific immunoglobulin fraction separated by successive affinity chromatography on Protein-A-Sepharose and leptin-Sepharose columns according to standard methods. The purified polyclonal as well as monoclonal antibodies must be then characterised for specificity and lack of cross-reactivity with related molecules as much as possible. This could be easily performed by standard methods using labelled leptin (e.g., with radioisotopes or biotin) as tracer in competition with increasing levels of unlabeled potential cross-reactants for antibody binding. In some cases, further purification may be required to obtain highly specific antibody fraction or for selection of higher affinity antibody fraction from a polyclonal pool. In the case of monoclonal antibodies, care should be taken to select antibodies with good binding characteristic and specificity not only for the immunogen, but also for the native circulating molecules, particularly when recombinant molecule or peptide antigen are used for immunization. Antibodies demonstrating unacceptable yield, abnormal or highly differential response against immunogen vs native molecule should be rejected. Cross-reactivity studies may be further evaluated by other standard methods such as the well-established SDS-PAGE and Western immunoblot methods under reducing and non-reducing conditions. Evaluation of leptin immunoreactivity detected in serum samples fractionated by high performance liquid chromatography (HPLC) could be also used to roughly define the molecular weight profile of the immunoreactivity detected (22, 26).

Monoclonal antibodies may be prepared according to the well established standard laboratory procedures "Practice and Theory of Enzyme Immunoassays" by P. Tijssen (In Laboratory Techniques in Biochemistry and Molecular Biology, Eds: R. H. Burdon and P. H. van Kinppenberg; Elisevier Publishers Biomedical Division, 1985), which are based on the original technique of Kohler and Milstein (Kohler G., Milstein C. Nature 256:495, 1975). This is usually performed by removing spleen cells from immunized animals and immortalizing the antibody producing cells by fusion with myeloma cells or by Epstein-Barr virus transformation, and then screening for clones expressing the desired antibody, although other techniques may be also used.

EXAMPLE 11

Procedures for Antibody Coating to Microwells

Procedures for antibody (500 ng/100 uL/well) coating to microwells were as previously described (29-31). The same procedure was also used for CLBD coating to microwell, except that the effect of coating concentration and volume as well as using coating buffer pH in the 2.6 to 9.1 range were examined. The coating buffers with pH in the 2.6 to 6.5 range were made by titrating 0.1 M citric acid with 0.2 M dibasic sodium phosphate. Coating buffers pH 6.5, pH 8.5 and pH 9.1 were based on 0.2 M sodium phosphate, 0.05 M sodium borate, or 0.1 M sodium carbonate, respectively. Procedures for antibody conjugation to biotin or HRPO have been also described (29-31). Conjugation of CLBD to biotin was performed in a similar manner using 50 and 100 excess molar ratios of EZ-link sulfo-NHS-LC-LC biotin (Pierce, Rockford, Ill.). Standards were prepared by appropriately diluting recombinant human leptin into various standard matrixes at the desired concentration levels (ng/ml). The standard matrixes evaluated were normal goat serum, normal equine serum, normal goat serum and buffer-based standard matrix. The latter included diluent #1 [(50 mM Sodium Phosphate, pH 7.4 containing, 0.005 M sodium EDTA, and 1 g bovine serum albumin (BSA), 9 g NaCl, 1 mL Trasylol, and 2.5 mL Proclin-300 per litre] and diluent # 2 (similar to diluent 1, but containing 20 g BSA per litre) and their modifications. Because of the presence of leptin binding protein in the various sera, the assay response to leptin standards made in the standard matrix buffer containing 0% serum, 25% serum, 50% serum vs 100% serum matrix was also evaluated.

EXAMPLE 12

Potential Effect of Assay Buffer

In addition to the above parameters, the potential effect of the assay buffer formulations on binding response were also examined. Among the initial set of buffers, the followings were selected for further evaluations.

Buffer A. Fifty mM Trisma Maleate, pH 7.0, containing 0.001 M EDTA and 9 g NaCl, 5 g BSA, 0.5 mL Tween-20, and 2.5 mL Proclin-300 per liter.

Buffer B. Fifty mM Sodium Borate, pH 8.5, containing 9 g NaCl, 5 g BSA, 0.5 mL Tween-20, and 2.5 mL Proclin-300 per liter.

EXAMPLE 13

Assay Development

For assay development, the anti-leptin antibodies were purified using standard antibody purification schemes. Both monoclonal and polyclonal antibodies were purified by affinity chromatography over Protein-A columns and if necessary, by affinity chromatography over a gel column containing immobilized leptin. To evaluate the impact of assay design on performance, both one-step (simultaneous incubation of sample plus detection antibody or CLBD-biotin tracer) and two-step (sequential incubation of sample and the detection antibody or CLBD-biotin tracer) configurations were assessed. Based on such experimentation, assay designs involving solid-phase capture receptor and liquid-phase detection antibody appeared more promising. The capture receptor, in this case CLBD, may be linked to various supports by the standard non-covalent or even covalent binding methods, depending on the analytical as well as clinical requirements of the assay. The solid-support might be in forms of test tubes, beads, microparticles, filter paper, membranes, glass filter, magnetic particles, silicon chip, or materials and approaches known to those skilled in the art. The use of microparticles, particularly magnetizable particles that have been directly coated with the receptor (magnetic particles-capture receptor) or particles that have been labelled with a universal binder (e.g., avidin or anti-receptor antibody) are ideal for significantly shortening the assay incubation time. This along with other alternative approaches known to others may allow for assay completion within minutes without limiting the required sensitivity of the assay. The use of magnetizable particles or similar approaches would also allow for convenient automation of the technology on the widely available immunoanalyzers. Obviously, the assay sensitivity could be improved by using other immunoassay detection systems, including but not limited to luminometric, electrometric, and their various, modifications, and combinations.

The antibody used for leptin detection may be either directly labelled to a reported molecule, or detected indirectly by a secondary detection system. The latter may be based on several different principles, including antibody recognition by a labelled anti-species antibody or other forms of immunological or non-immunological bridging and signal amplification detection systems (e.g., the biotin-streptavidin technology). The signal amplification approach may be used to significantly increase the assay sensitivity and improve low levels reproducibility and performance. The label used for direct or indirect antibody labelling may be any detectable reporter molecule. Examples of suitable labels are those widely used in the field of immunological and non-immunological detection systems. These may include fluorophores, luminescents, metal complexes and radioactive labels, as well as moieties that could be detected by other means (e.g., electrical) or suitable reagents such as enzymes and their various combinations and substrates.

The assay design may be homogeneous or heterogeneous, depending on particular application of the assay and the need for speed, sensitivity, accuracy and convenience. The detail discussion on helpful designs may be found in various immunoassay books and literatures, including "Practice and Theory of Enzyme Immunoassays" by P. Tijssen (In Laboratory Techniques in Biochemistry and Molecular Biology, Eds: R. H. Burdon and P. H. van Kinppenberg; Elisevier Publishers Biomedical Division, 1985),

EXAMPLE 14

Free Leptin Receptor-Mediated Enzyme Immunoassay (RMEIA)

Development of the free leptin RMEIA was based on systematic evaluation of one-step and two-step assay configurations involving solid-phase antibody or CLBD capture with liquid phase CLBD tracer or antibody detection, respectively. Approaches affording reasonable response were selected for further evaluation and optimisation. Guided by the performance data, the version of the RMEIA presented in this report involves addition of standards, samples or controls (0.05 mL) and the detection antibody (0.05 mL), in duplicate, to CLBD pre-coated microwells, followed by 4 hr incubation at room temperature. The wells are washed ×5, incubated with 0.1 mL/well TMB/$H_2O_2$ substrate solution for 15-min. Stopping solution (0.1 mL) is then added and absorbance is measured by dual wavelength measurement at 450 nm with background wavelength correction set at 620 nm. A set of recombinant human leptin standards is included in each run against which, the unknown sample values are quantified colorimetrically. Obviously any and all sample and antibody volumes and incubation times could be altered as may be seen appropriate. The latter could include modifications used in conventional immunoassays or alternative approach known to those skilled in the art.

In the present formulation of the Free Leptin RMEIA, the assay buffer was assay buffer B (0.05 mol/L borate, pH 8.5, 9 g/L NaCl, 1 g/L bovine serum albumin (BSA), 50 ml/L normal goat serum, 0.5 ml Tween 20, 5 mL/L proclin 300). The standard matrix was 50 mM sodium phosphate, pH 7.4 containing, 0.005 M sodium EDTA, and 1 g bovine serum albumin (BSA), 9 g NaCl, 400 mL goat serum, 1 mL Trasylol, and 2.5 mL Proclin-300 per liter. Where indicated standard matrix containing different concentrations of goat serum or serum from other animal species, including 100% serum matrix may be used. Based on the outcome of coating pH trials, coating of CLBD to microwells was performed at slightly acidic pH, using 0.2M Sodium Phosphate, pH 6.5. In brief, 0.2 mL of the CLBD re-suspended in the coating buffer at a concentration of 5 ug/mL was added into each microwell and allowed to incubate overnight at room temperature. The wells were then washed ×1 with the wash solution and 0.2 mL/well of the blocking solution was added and allowed to incubate for 1 hr as above. The wells were washed ×1 prior to use or stored for up to 2 days in the blocking buffer at 4° C. The stopping solution was 0.2 mol/L sulfuric acid in deionised water. The composition of the coating and blocking buffers as well as the wash solution were as described previously (29, 30).

Coupling of the detection antibodies to HRP was performed as described (29, 30). The coupling reaction involved activation of the enzyme with sulfo-SMCC and its subsequent conjugation to the anti-leptin antibody, which had been activated by 2-iminothiolane. The stock HRP-conjugated antibody solution was diluted at least 1000-fold prior to use. Free Leptin standards were prepared by diluting recombinant human leptin in the standard matrix buffer described above to give the required leptin reference standard values of about 0.5 to 100 ng/mL. The standards were freshly prepared prior to use. The quality control samples used were fresh serum samples containing various levels of leptin. The nominal concentrations of the control samples were established by analyzing the samples in a conventional Leptin ELISA.

EXAMPLE 15

Free Leptin RMEIA Validation Procedures

The intra-assay CVs was determined by replicate analysis of 4 samples in one run; inter-assay CVs by duplicate measurement of four samples in 9 separate runs. Specificity was assesses by the various approaches described in the Results section. For comparative evaluations, random adult male and female samples were assayed by the present Free Leptin RMEIA and by commercially available ELISAs for total leptin or soluble leptin receptor (DSL, Webster, Tex.). All values are means of duplicate measurements.

EXAMPLE 16

Comparative Assay Studies

For comparative studies, well-established commercial ELISA developed by DSL (Webster Tex.) for determination of total leptin and soluble leptin receptor were used. These assays are based on one- or two-step non-competitive immunoassay principals and involve capture/detection antibodies highly specific for leptin and the soluble leptin receptor (33).

EXAMPLE 17

Data Analysis

The RMEIA and ELISA results were analyzed using the data reduction packages included in the Labsystems Multiskan microplate ELISA reader (Labsystems, Helsinki, Finland) with cubic spline (smoothed) curve fit. Linear regression analysis was performed by the least square method and correlation coefficients were determined by the Pearson method. The plots and statistical were performed by Sigma-Plot and SigmaStat (Superior Performing Software Systems Inc, Chicago Ill. 60606-9653).

EXAMPLE 18

Antibody Capture vs. Receptor Capture Approach

In the preliminary assessment of various possibilities, one- or two-step assay configurations performed in antibody (solid-phase antibody capture) or receptor (solid-phase receptor capture) coated microwells were evaluated. Protocol selection was initially based on the relative binding response of the various assay formats as well as non-specific binding signal (NSB) generated by the zero-dose standard. Based on the outcome of the binding studies, the antibody-capture approach was rejected because of poor signal/dose ratios at various leptin concentration as well as high NSB (Table 3). The antibody-capture format evaluated in some details involved incubation of sample (50 uL) and assay buffer (50 uL) in antibody coated wells followed by sequential washing and incubation with CLBD-biotin tracer, streptavidin-HRPO, and colorimetric quantification. The uses of strategies commonly known to minimize NSB were found ineffective.

TABLE 3

| Leptin | Free Leptin RMEIA; Antibody Capture | | | | |
|---|---|---|---|---|---|
| | Anti-Leptin Antibody (OD) | | | | |
| ng/mL | 6B4B | 6B4E | BC4B | 6D26 | ELISA Plate |
| 0 | 0.46 | 0.38 | 1.51 | 0.38 | 0.81 |
| 25 | 0.44 | 0.38 | 1.68 | 0.41 | 0.85 |
| 50 | 0.42 | 0.39 | 1.85 | 0.39 | 0.77 |
| 100 | 0.48 | 0.39 | 1.98 | 0.39 | 0.78 |

Two-step assay: 50 uL sample + 50 uL assay buffer, incubate 3 h Add CLBD-biotin (100 uL, 25 ng/mL), incubate 1 h; Add steptavidin (SA)-HRPO (100 uL, 50 ng/mL), incubate 15 min, Add TMB substrate (100 uL), incubate 10 min; Add stopping solution (100 uL), read absorbance at 450 nm

EXAMPLE 19

Receptor-Capture Approach

In the preliminary trials, a series of experiments was performed to evaluate, identify, and optimize potential factors that could improve performance of the assay. Attention was particularly given to modifications capable of minimizing zero-dose standard NSB signal, while maintaining high signal/dose ratios. The initial experiments identified the importance of standard preparation and storage as well as the processing of CLBD coated plates. The assay signal was found to be significantly higher in response to freshly prepared leptin standards than standards stored for 48 hrs at 4 C. Similarly, there was a gradual decrease in the assay response when wet coated plates (containing blocking buffer) were stored at 4 C for more than 3 days (data not shown). Collectively, the data indicated the impact of standard preparation and plate coating process and suggested providing the standards and plates in lyophilized and dry format, respectively.

EXAMPLE 20

Impact of Receptor Coating pH

Initial experiments identified the importance of coating buffer in binding response. This was then followed by comparative evaluation of the effectiveness of the various detection antibodies and pH of coating CLBD to microwells. As represented in Table 4, the assay signal was significantly higher for receptor coating at pH 6.5, particularly when used in combination with the polyclonal anti-leptin antibody labeled with HRPO or biotin. Similar to the reduced assay signal for plates coated at lower coating pH (Table 4), signal loss was also evident when coating at higher (>7.0) pH (data not shown). Based on these and similar observations, 0.2 M sodium phosphate buffer, pH 6.5, was selected for CLBD coating to microwells.

TABLE 4

| | Free Leptin RMEIA; CLBD Coating | | | | | | | | | |
|---|---|---|---|---|---|---|---|---|---|---|
| Leptin | Antibody (Ab)-HRPO | | | | | Antibody (Ab)-Biotin | | | | |
| ng/mL | pH 2.6 | pH 3 | pH 4 | pH 5 | pH6.5 | pH 2.6 | pH 3 | pH 4 | pH 5 | pH6.5 |
| 0 | 0.14 | 0.12 | 0.09 | 0.12 | 0.09 | 0.41 | 0.18 | 0.22 | 0.31 | 0.32 |
| 25 | 0.15 | 0.12 | 0.16 | 0.22 | 0.19 | 0.43 | 0.28 | 0.67 | 1.16 | 1.45 |

TABLE 4-continued

Free Leptin RMEIA; CLBD Coating

| Leptin | Antibody (Ab)-HRPO | | | | | Antibody (Ab)-Biotin | | | | |
|---|---|---|---|---|---|---|---|---|---|---|
| ng/mL | pH 2.6 | pH 3 | pH 4 | pH 5 | pH6.5 | pH 2.6 | pH 3 | pH 4 | pH 5 | pH6.5 |
| 50 | 0.14 | 0.14 | 0.19 | 0.28 | 0.28 | 0.44 | 0.38 | 0.95 | 1.71 | 2.26 |
| 100 | 0.21 | 0.14 | 0.26 | 0.37 | 0.48 | 0.39 | 0.41 | 1.34 | 2.38 | 2.87 |

Two-Step assay protocol using goat anti-leptin detection antibody labelled with HRPO or Biotin
Sample (25 uL) + assay buffer (50 uL), incubate 4 h; Add Ab-HRPO (100 uL) or Ab-biotin, incubate 1 h Add SA-HRPO and complete the assay colorimetrically as described in footnote to Table 1.

EXAMPLE 21

Biotinylated vs. HRPO-Antibody Detection

The potential impact of antibody labeling was further assessed by comparison of standard curve characteristics and other assay parameters using biotin or HRPO detection. The initial observations identified significant improvement in signal with antibody biotinylation, but at the expense of relatively high NSB signal (Table 4). As limiting NSB to levels seen for samples with very low total leptin levels was important for improving the lower limit of detection and accuracy, the impact of a number of assay variables (standard matrix, assay buffer, coating and detection antibody concentration) were systematically examined. As represented in Table 5, the major improvement was achieved by using HRPO-labeled detection antibody as signal (particularly with 200 uL/well coating) was comparable to levels obtained with the biotinylated antibody, while the NSB of the zero-dose standard was significantly minimized. The HRPO-antibody detection system was therefore selected for further evaluations.

EXAMPLE 22

Importance of Standard Matrix: One- vs Two-Step Assay Format

In immunoassays, particularly in receptor mediated systems, the standard matrix should be as close as possible to sample matrix so that differential effects of standard vs sample response are minimized. Accordingly, comparative analysis of signal generated for standards prepared in different buffers and in various animal sera was performed. As expected, the receptor-mediated one- and two-step assay formats responded differently to the various standard matrixes, with the serum-based standards generating a significantly lower binding response than the similarly prepared and tested buffer-based standards (Table 6). In addition, the use of serum-based standards, particularly in a one-step configuration, appeared highly advantageous in terms of NSB signal of the zero-dose standard and signal/dose ratios. It is important to note that the free leptin levels obtained by the one-step assay format using the serum-based standards were significantly higher and were within the immunoassay range for plasma free leptin (22-24). On the other hand, the comparatively high assay response for the buffer-based standards resulted in both high NSB as well as low sample readings in both assays, particularly in the two-step format (Table 6).

TABLE 5

CLBD Coating, Effect of Various Assay Variables

| | Ab-Biotin | | | | Ab-HRPO | | | |
|---|---|---|---|---|---|---|---|---|
| | Standard Diluent | | | | | | | |
| | Diluent 1 | | Diluent 2 | | Diluent 1 | | | |
| | Assay Buffer | | | | | | | |
| | A | B | A | B | A | B | A | B |
| | CLBD Coating | | | | | | | |
| Leptin (ng/ml) | 100 uL/well | | | | 100 uL/well | | 200 uL/well | |
| 0 | 1.12 | 0.88 | 1.05 | 0.88 | 0.07 | 0.08 | 0.09 | 0.09 |
| 25 | 1.82 | 1.59 | 1.51 | 1.45 | 0.66 | 0.79 | 0.79 | 0.89 |
| 50 | 2.4 | 2.11 | 1.89 | 1.76 | 1.09 | 1.32 | 1.32 | 1.35 |
| 100 | 2.9 | 2.79 | 2.46 | 2.41 | 1.55 | 1.89 | 2.05 | 2.41 |

Two-Step assay was carried out as described in footnote to Table 2.
The standard diluent 1 and 2, and Assay buffer A and B are described in the Materials and Methods section.
CLBD coating concentration was 10 ug/ml coated at 100 or 200 uL/microwell.

TABLE 6

Free Leptin RMEIA; Two-Step Vs One-Step

| | One-Step (OD) | | Two-Step (OD) | |
|---|---|---|---|---|
| | Diluent 1 | NGS | Diluent 1 | NGS |
| ng/mL Leptin | Standard Matrix | | | |
| 0 | 0.074 | 0.018 | 0.128 | 0.088 |
| 3.13 | 0.322 | 0.051 | 0.183 | 0.102 |
| 6.25 | 0.569 | 0.089 | 0.241 | 0.116 |
| 12.5 | 1.021 | 0.165 | 0.357 | 0.155 |
| 25 | 1.905 | 0.333 | 0.583 | 0.241 |
| 50 | 2.739 | 0.537 | 0.989 | 0.365 |
| 100 | 3.181 | 0.712 | 1.589 | 0.569 |
| Sample | Free Leptin (ng/mL) | | | |
| 1 | ND | 4.5 | ND | ND |
| 2 | ND | 4.9 | ND | ND |
| 3 | 8.7 | 101 | ND | 9.8 |
| 4 | 10.1 | 145 | ND | 8.9 |
| 5 | 4.5 | 35.6 | ND | 3.3 |
| 6 | 5.8 | 47.1 | ND | 5.8 |
| 7 | 8.9 | 112 | ND | 11.3 |

Two-Step assay was carried out as described in footnote to Table 2.
One-Step assay was done by simultaneous incubation of sample and HRPO-Ab for 4 h followed by colorimetric signal development.

EXAMPLE 23

Receptor-Mediated Free Leptin Enzyme Immunoassay (RMEIA)

Because of the apparent advantages of the one-step RMEIA, particularly its allowance for low NSB, the assay response to a number of variables, including sample volume, incubation time, and standard matrix composition was evaluated. As shown in Tables 6 and 7, the one-step assay was comparatively more sensitive than the two-step RMEIA, with the binding signal reaching near plateau after about 2 h of incubation (Table 7). Similarly, the importance of differential matrix effect and, thus, changes in absolute sample readings was evident when the assay response to standard preparation containing different amount of goat serum (0-100%) was examined. In accordance with results outlined above (Table 6), there was a significant increase in standard signal in response to decreasing serum content of the standard matrix, resulting in the expected decrease in the absolute levels of the corresponding samples (Table 8). As the performance of the one-step assay, particularly in terms of sample readings and NSB signal of the zero-dose standard, appeared acceptable, a one-step receptor-mediated assay protocol for free leptin, incorporating the various improvements was developed. In the assay, sample (50 uL) and HRPO-labeled detection antibody (50 uL) are incubated for 4 h in CLBD-coated microwells at room temperature. After washing, TMB substrate is added and after 15-min incubation, the reaction is developed colorimetrically.

TABLE 7

One-Step Free Leptin RMEIA

| Leptin | Incubation Time (450 nm Absorbance) | | | | |
|---|---|---|---|---|---|
| ng/mL | 1 h | 2 h | 3 h | 4 h | 5 h |
| 0 | 0.09 | 0.15 | 0.17 | 0.21 | 0.25 |
| 3.13 | 0.31 | 0.54 | 0.61 | 0.76 | 0.88 |
| 6.25 | 0.55 | 0.96 | 1.1 | 1.27 | 1.49 |
| 12.5 | 1.09 | 1.84 | 1.98 | 3.36 | 2.41 |
| 25 | 2.16 | 3.09 | 3.12 | 3.49 | 3.34 |
| 50 | 3.12 | 3.19 | 3.37 | 3.45 | 3.35 |
| 100 | 3.61 | 3.54 | 3.29 | 3.24 | 3.32 |

Sample (100 uL) and Ab-HRPO (50 uL) incubated as shown.
Reaction developed colorimetrically.

TABLE 8

One-Step Free Leptin RMEIA

| | 100% GS | 50% GS | 25% GS | 0% GS |
|---|---|---|---|---|
| ng/mL Leptin | Standard Matrix (OD) | | | |
| 0 | 0.026 | 0.032 | 0.039 | 0.091 |
| 3.12 | 0.047 | 0.083 | 0.137 | 0.255 |
| 6.25 | 0.069 | 0.161 | 0.246 | 0.481 |
| 25 | 0.208 | 0.566 | 0.805 | 1.533 |
| 50 | 0.431 | 0.868 | 1.457 | 2.471 |
| 100 | 0.677 | 1.237 | 2.046 | 3.045 |
| Sample | Free Leptin (ng/mL) | | | |
| 1 | 11.2 | 3.7 | 2.1 | 0.53 |
| 2 | 34.6 | 12.7 | 8.3 | 3.89 |

TABLE 8-continued

One-Step Free Leptin RMEIA

| | 100% GS | 50% GS | 25% GS | 0% GS |
|---|---|---|---|---|
| 3 | 13.3 | 4.5 | 2.6 | 0.79 |
| 4 | 26.9 | 9.6 | 6.2 | 2.47 |

Free Leptin assay performed by incubating sample (50 uL) and Ab-HRPO in CLBD coated wells (5 ug/mL, 200 uL/well) for 4 h.
Samples contained 11-40 ng/mL total leptin immunoreactivity.

The selected RMEIA protocol demonstrated acceptable analytical performance characteristics. As shown in Table 9 and Table 10, the overall intra- and inter-assay imprecision of the assay was similar to levels seen for conventional immunoassays and were in general better than 10%

TABLE 9

Free Leptin RMEIA

Intra-assay Imprecision

| Sample | Mean | SD | % Cv | n |
|---|---|---|---|---|
| 1 | 11.29 | 0.988 | 8.8 | 8 |
| 2 | 15.03 | 0.824 | 5.4 | 8 |
| 3 | 37.5 | 3.73 | 9.9 | 8 |
| 4 | 64.6 | 3.33 | 5.2 | 8 |

TABLE 10

Free Leptin RMEIA

Inter-assay Imprecision Sample

| | I | II | III | IV |
|---|---|---|---|---|
| | 12.1 | 16.1 | 37.5 | 71.2 |
| | 10.7 | 14.9 | 38.1 | 68.9 |
| | 10.7 | 16.2 | 36.9 | 63.3 |
| | 8.8 | 13.6 | 37.9 | 70.6 |
| | 10.8 | 16.1 | 38.9 | 64.8 |
| | 10.9 | 15.1 | 38.1 | 63.9 |
| | 10.7 | 16.1 | 38.9 | 63.4 |
| | 10.8 | 15.2 | 35.6 | 62.3 |
| | 11.4 | 16.4 | 38.9 | 64.5 |
| Mean | 10.8 | 15.5 | 37.9 | 65.9 |
| SD | 0.87 | 0.91 | 1.09 | 3.4 |
| % CV | 8.1 | 5.8 | 2.9 | 5.2 |

EXAMPLE 24

Specificity Studies

In addition to the specificity advantages of employing CLBD as the principal leptin binder, the specificity of the assay for free leptin was assessed by different approaches as follows:

a). Receptor Binding Inhibition. In this experiment, a given concentration of human leptin falling within the assay range (35.9 ng/ml) was mixed with increasing amounts of CLBD. After 2-hr incubation at room temperature, the various mixtures were assayed for free leptin by the present Free Leptin RMEIA. Results are expressed as % free leptin recovery in response to pre-incubation with increasing receptor concentrations. Consistent with specificity for free leptin, there was a gradual decrease in free leptin levels in response to pre-incubation with increasing concentrations of the receptor (Table 11).

TABLE 11

Free Leptin RMEIA Specificity

| CLBD Added ng/mL | Free Leptin | | |
|---|---|---|---|
| | Expected ng/mL | Found ng/mL | Recovery % |
| 0 | 35.9 | 35.9 | 100 |
| 50 | 35.9 | 25.1 | 69 |
| 250 | 35.9 | 10.5 | 29 |
| 500 | 35.9 | 5.1 | 14 |
| 2500 | 35.9 | 0.56 | 1.5 |
| 5000 | 35.9 | 0 | 0 |

All preparations were made in standard diluent #1
Assay was performed as described in Materials and Methods b). Sample Mixing Experiment. A serum sample containing relatively high free leptin (15.8 ng/mL) and relatively low soluble leptin receptor (19.4 ng/mL) was differentially mixed with another serum sample containing high soluble leptin receptor (96.7 ng/mL) and low free leptin (0.24 ng/mL). After overnight incubation at 4 C, the various mixed and unmixed samples were assayed for free leptin. Results are expressed as % free leptin recovery. The experiment was obviously based on the assumption that the soluble leptin receptor in the high receptor sample was at least partly unoccupied so that its addition to the high free leptin sample would result in somewhat lower than expected free leptin reactivity. According to published reports, up to 99% of the total soluble leptin receptor could be pre-occupied by endogenous leptin (34) and as such would be ineffective in mixed experiments describe here. However, as shown in Table 12, there was an obvious decrease in the expected free leptin levels in response to mixing, suggesting undetectability of the portion of the free leptin that had bound to the unoccupied soluble leptin receptors. In addition, as in the above experiment, the decreasing trend in the free leptin levels indicates insusceptibility of the present assay design to possible leptin dissociation from endogenous leptin bound complexes.

TABLE 12

Free Leptin RMEIA Specificity

| SLR Added ng/mL | Free Leptin | | |
|---|---|---|---|
| | Expected ng/mL | Found ng/mL | Recovery % |
| 0 | | 16.3 | |
| 19.3 | 13 | 12.8 | 98 |
| 39.4 | 9.8 | 6.8 | 69 |

Figure 11:
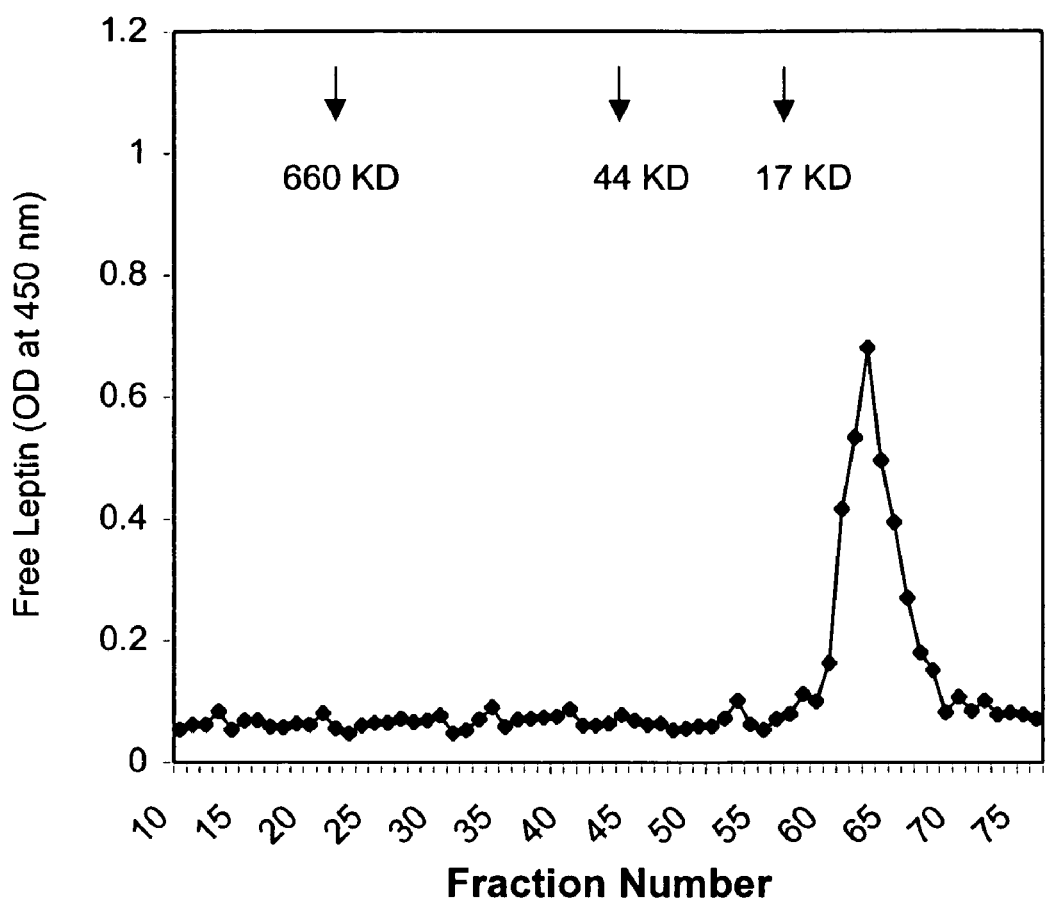
FIG. 11 illustrates a high-performance liquid chromatography (HPLC) profile of free leptin. A fresh serum sample was fractionated and fractions were assayed for free leptin reactivity by the Free Leptin RMEIA described herein. The column flow rate was 0.5 mL/min and 0.5 mL fractions were collected. Arrows mark the elution peak of the gel filtration molecular weight markers.

A sample with high free leptin and low soluble leptin receptor was mixed with another sample containig high soluble leptin receptor. Samples assayed by the Free Leptin RMEIA after overnight incubation.

c). HPLC Profile of Leptin Reactivity. Assay specificity was further examined by evaluating the gel filtration profile of leptin reactivity detected in serum. In initial trials, serum samples containing high endogenous free leptin levels were fractionated by size exclusion HPLC and the fractions assayed for free leptin by the present Free Leptin RMEIA. As represented in FIG. 11, the free leptin reactivity invariably eluted in single peak in the 10-20 KD molecular weight region.

Figure 12:
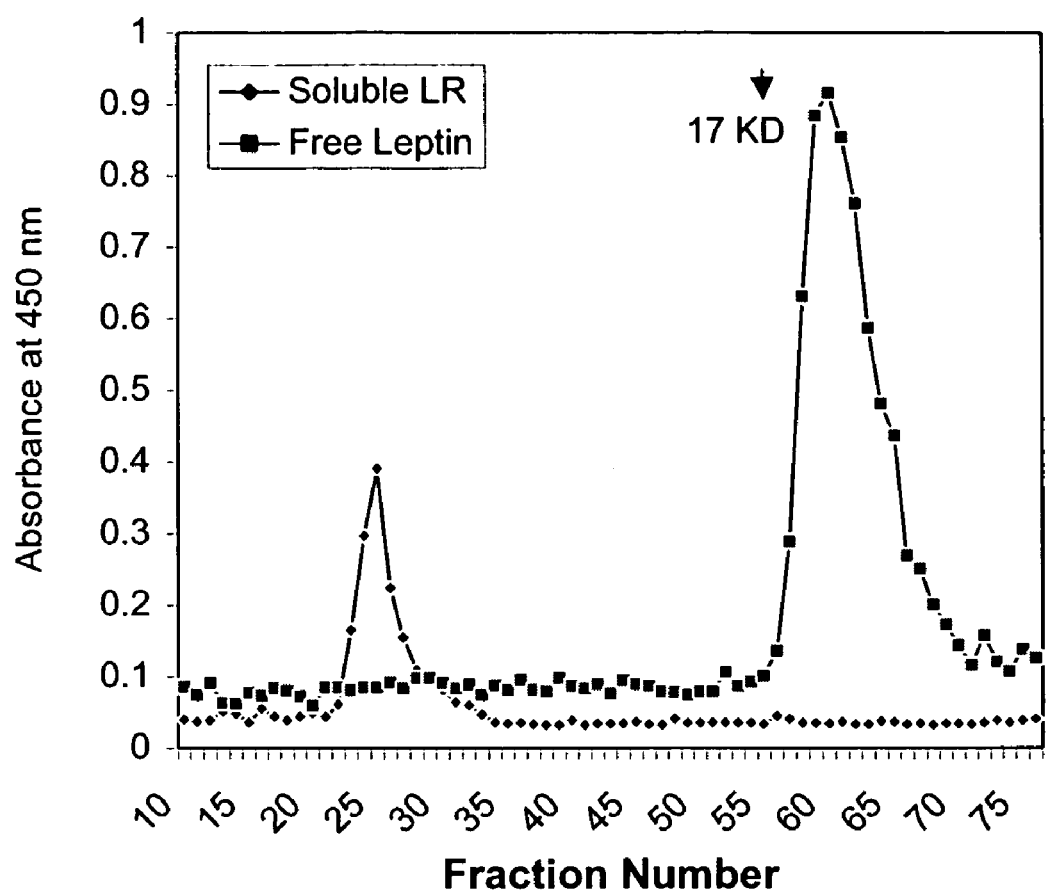
FIG. 12 illustrates an HPLC profile of soluble leptin receptor and free leptin. A fresh serum sample containing 200 ng/mL soluble leptin receptor was pre-incubated overnight with 400 ng/mL exogenous leptin, fractionated as in FIG. 11, and fractions were assayed for soluble leptin receptor and free leptin. Arrows mark the elution peak of the gel filtration molecular weight markers.

In further assessments, a serum sample containing high endogenous soluble leptin receptor was fractionated as above and fractions assayed for free leptin and soluble leptin receptor HPLC profile. Results identified elution of soluble leptin receptor immunoreactivity and free leptin reactivity in the expected ~300 KD (33) and ~15 KD regions (26), respectively (data not shown). Because of the possibility of low leptin occupancy of the endogenous soluble leptin receptor, the serum sample was overnight incubated with excess recombinant leptin (300 ng/ml) and rechromatographed. As represented in FIG. 12, the free leptin reactivity detected by the present assay was evident in a single peak eluting in the same molecular weight region as above. Again, no free leptin reactivity in fractions containing the soluble leptin receptor was detectable.

EXAMPLE 25

Comparative Studies

Figure 13:
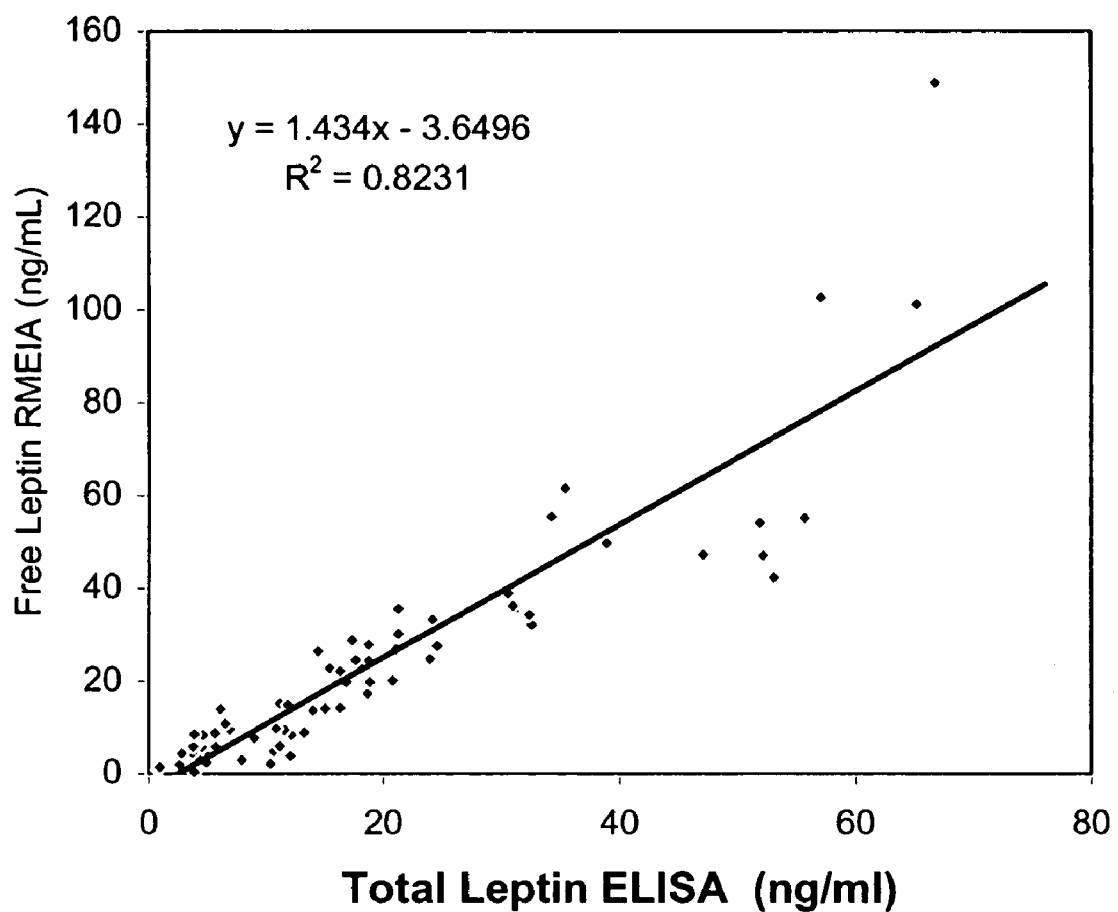
FIG. 13 illustrates a comparison of free leptin RMEIA with total leptin ELISA. A randomly selected population of adult male and female clinical samples (n=69) were assayed for total leptin by DSL Leptin ELISA and by the present Free Leptin RMEIA. Values are means of duplicate measurements. RMEIA leptin standards were prepared in normal goat serum.
Figure 14:
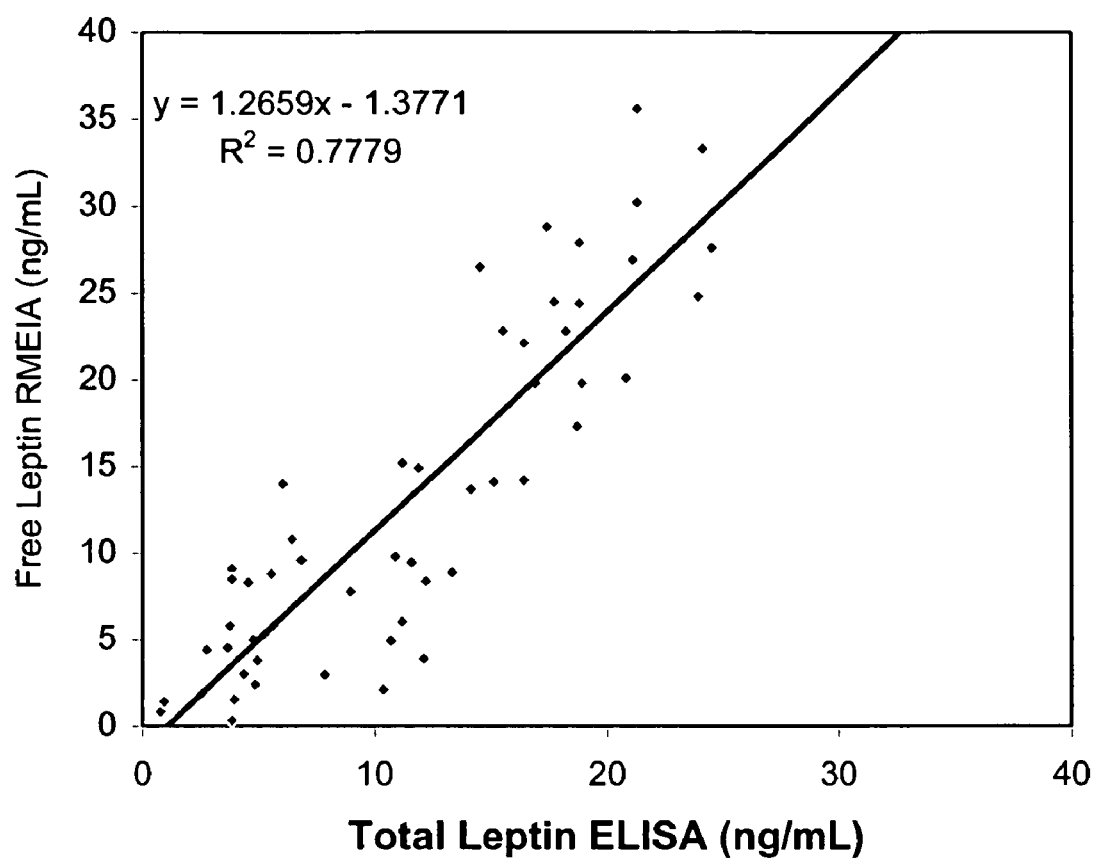
FIG. 14 illustrates a comparison of free leptin RMEIA with total leptin ELISA in samples with total leptin of less than 25 ng/mL. The figure shows the expanded relationship between the corresponding sample values depicted in the lower region of FIG. 3. RMEIA leptin standards were prepared in normal goat serum. Values are means of duplicate measurements.
Figure 15:
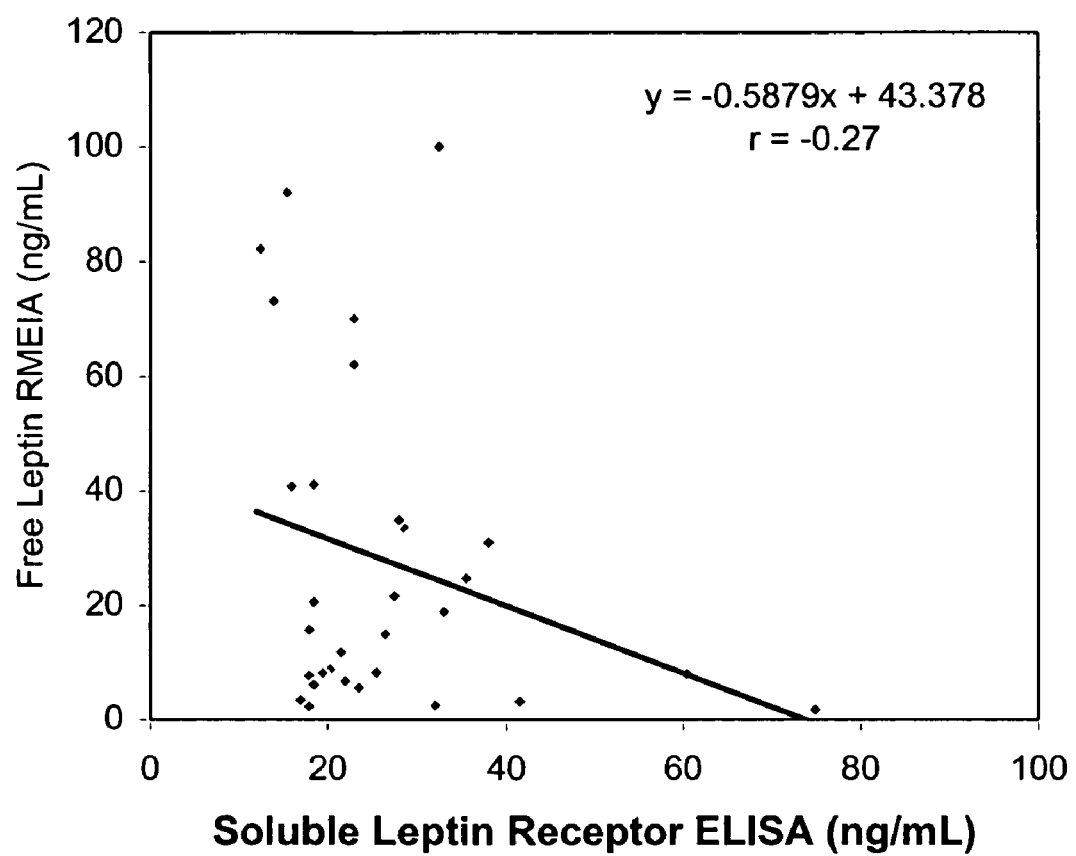
FIG. 15 illustrates a relationship between free leptin and soluble leptin receptor. A randomly selected population of adult male and female clinical samples (n=31) were assayed by the present Free Leptin RMEIA and by a commercial Soluble Leptin Receptor ELISA. Values are means of duplicate measurements.

In comparative studies of randomly selected serum samples from a clinical population of adult subjects, the free leptin levels measured by the present RMEIA correlated strongly with total leptin quantified by a commercially ELISA (DSL, Webster, Tex.) (FIG. 13). However, despite the expected positive relationship, there was significant scattering of the measured values around the regression line, particularly at lower leptin levels (FIG. 14) where higher proportions of plasma leptin are reportedly in the bound form (22, 34). As might be expected, the circulating free leptin levels correlated inversely with the corresponding concentrations of the soluble leptin receptor (FIG. 15).

Discussion

The importance of precise and accurate determination of free leptin is linked to its apparent pathophysiological relevance and potential diagnostic and therapeutic applications. In addition to regulating feeding behavior and energy metabolism, recent evidence has broadened the potential scope of the leptin/leptin receptor system to include a diversity of other biological processes (3, 4, 9-11). Collectively, the balance of leptin bioavailability appears to be influenced by a complex array of nutritional and hormonal factors as well as being affected by circulating levels of binding proteins and soluble leptin receptors. (8, 9, 11-13). The complexity of factors affecting leptin bioavailability is further evident by the wide range and overlapping concentrations of plasma leptin and soluble leptin receptor in normal vs obese individuals, and the extend of receptor occupancy by leptin as a function of obesity and body mass index (14-18, 34). In this context, development of simple and specific methodologies for free leptin may provide a more accurate measure of leptin bioavailability, and thus its state of bioactivity, and a more pathophysiologically relevant measure of leptin association with disease.

The limited methodology currently described for free leptin are either based on determination of leptin mass by conventional non-competitive immunoassay approach (27), or are based on interaction of plasma leptin with cell surface receptors in quantitative in vitro assays (28). Although the later is capable of function leptin determination, the procedure is both expensive and highly inconvenient. Determination of leptin mass by the conventional "sandwich-type" ELISAs (27) are also highly prone to leptin dissociation from the leptin bound complexes and the measurements could readily include assay response to both functional (capable of receptor binding) and non-functional leptin variants. The innovative receptor-mediated approach described in this report combines the specificity of CLBD for leptin with immunological leptin detection, thus relying on both functional integrity as well as immunological reactivity for accurate determination of free (bioavailable and bioactive) leptin. The simplified RMEIA protocol has the added advantages of being conveniently applicable to various manual or automated applications.

The free leptin RMEIA, an immunofunctional assay, involves a recently validated chicken leptin binding peptide that specifically binds to free (bioactive) leptin as well as allowing for leptin detection by an antibody-directed approach. Fundamentally, the combination of receptor binding and immunological detection of bound leptin is an improtant measure of assay specificity. However, the latter was further demonstrated by complete inhibition of the binding activity in response to leptin pre-incubation with increasing concentrations of CLBD (Table 11). The substantiating specificity data was also indicated by differential mixing of samples with high endogenous soluble leptin receptor with samples containing high free leptin (low receptor) and analyzing the effect on free leptin determinations. Although, a gradual decrease in free leptin levels in response to increasing levels of endogenous soluble leptin receptor addition was observed, the inhibition was not as complete as described above. The lack of complete inhibition (Table 12) is most possibly due to the high occupancy levels of the circulating soluble leptin receptors by endogenous leptin (50-100%), particularly in obese subjects (34).

Figure 2:
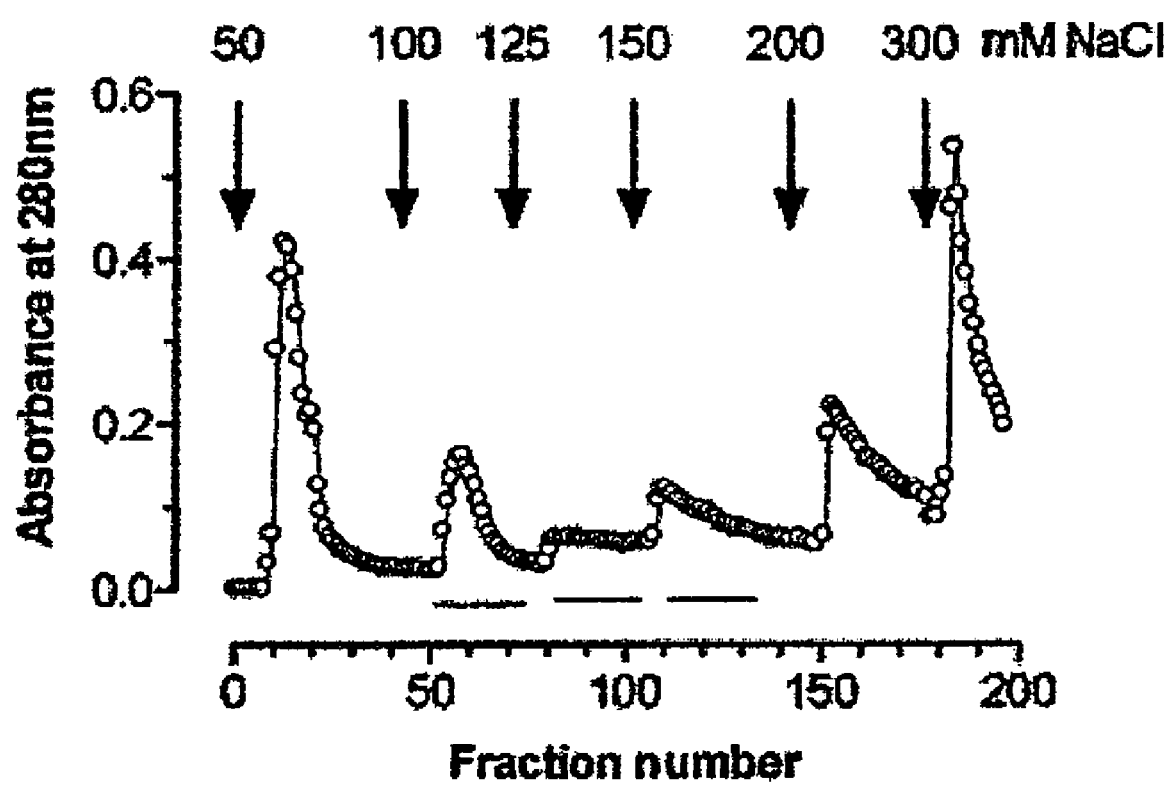
FIG. 2 illustrates a purification of hLBD extracted and refolded from inclusion bodies on a Q-Sepharose column. The column (2.5×7 cm) was equilibrated with 10 mM Tris-HCl, pH 9.0, at 4° C. The dialyzed solution of refolded protein was applied to the column at a rate of 120 ml/h. Elution was carried out using a discontinuous NaCl gradient in the same buffer at 120 ml/h, and 5-ml fractions were collected. Protein concentration was determined by absorbance at 280 nm. Every fifth tube was assayed for hLBD content by gel filtration in a Superdex™75 HR column (see text). Tubes 51-75, 78-104, and 110-135 were pooled (pools 100, 125, and 150 mM, respectively).
Figure 3:
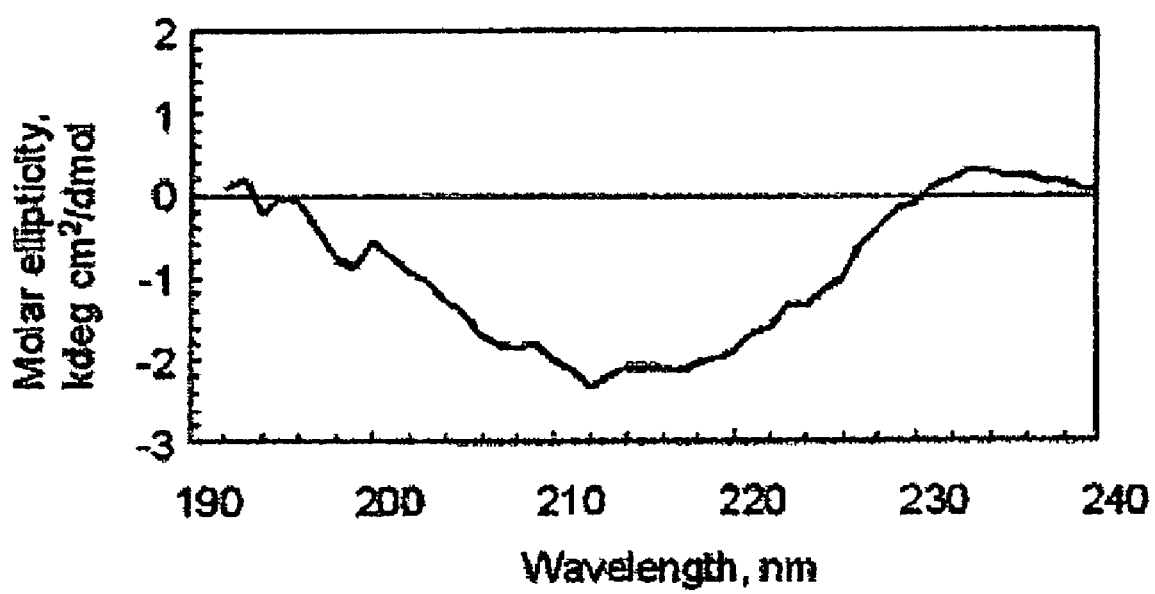
FIG. 3 illustrates a circular dichroism (CD) spectrum of purified recombinant leptin-binding domain in 65 mM sodium carbonate buffer, pH 7.5.

As expected, in a series of size fractionation experiments by HPLC, plasma leptin reactivity by the present RMEIA eluted in a single peak corresponding to the molecular weight of free leptin (FIG. 1). In contrast, there was no free leptin reactivity in HPLC fractionated samples that contained the soluble leptin receptor (data not shown). Because the latter observation might have been influenced by the extent of soluble leptin receptor occupancy by endogenous leptin (34), the above sample was overnight incubated with excess exogenous leptin (400 ng/mL) and rechromatographed. As shown in FIG. 2, binding activity by RMEIA was again evident in the free leptin molecular weight range with no demonstrable activity in fractions containing the soluble leptin receptor.

Finally, the observation of high correlation between free and total leptin is expected as circulating levels of both variants are directly related to body mass index (24-27). However, the significant scattering of the measured levels around the regression line, particularly at lower leptin levels (FIG. 4) where higher proportions of plasma leptin are reportedly in the bound form (22, 34), is indicative of the differential impact of assay specificity for free vs bound leptin. The latter, which could be considered an inactive variant of leptin pool, appears to be differentially detected by the available total leptin assays (26), thus, further complicating specificity of leptin determinations. As might be expected (26), the free leptin measured by the present RMEIA correlated inversely with the corresponding levels of the soluble leptin receptors. In this case (FIG. 5), the lowest free leptin levels were observed for samples that contained high concentrations of soluble leptin receptors, again exemplifying conditions where determination of free leptin might be of significant benefit. The latter is highly relevant given the finding that nearly 15-50% and 50-100% of the soluble leptin receptors in normal and in obese subjects circulates, respectively, in complex forms with the endogenous leptin (34).

In summary, we here report development of simple and specific receptor-mediated enzyme immunoassay (RMEIA) for accurate determination of free (bioactive) leptin. The assay, involving a recombinant chicken leptin receptor binding protein domain (CLBD) in concert with an enzyme-labeled anti-leptin detection antibody, is considered highly advantageous in expediting leptin investigations at both research and application levels. The method involves capturing the free leptin with CLBD coupled to a solid-phase and detecting the captured free leptin with an antibody coupled to a detection system. The present assay configuration optimized for the various contributing variables could be obviously modified using different approaches known to those skilled in the art.

The following references are cited herein.

1. Zhang y, Proenca R, Maffei M, Barone M, Leopold L, Rodier III W I. 1994 Positional cloning of the mouse obese gene and its human homologue. Nature. 372:425-432.
2. Considine R V, Sinha M K, Heiman M L, et al. 1996 Serum immunoreactive leptin concentrations in normal-weight and obese humans. N Engl J. Med. 344:292-295.
3. Bray G A, York D A. 1997 Leptin and clinical medicine: A new piece in the puzzle of obesity.
4. Tritos N A, Mantzoros C S. 1997 Leptin: its role in obesity and beyond. Diabetologica 40: 1371-1379.
5. Halaas J L, Gajiwala K S, Maffei M, et al. 1995 Weight reducing effects of the plasma protein encoded by the obese gene. Science. 269: 543-546.
6. Ogawa y, Masuzaki H, Isse N, et al. 1995 Molecular cloning of the rat obese cDNA and augmented gene expression in genetically obese Zucker fatty (fa/fa) rats. J Clin Invest. 96: 1674-1652.
7. Banks W A, Kastin A J, Huang W, et al. 1996 Leptin enters the brain by a saturable system independent of insulin. Peptides 17: 305-311.
8. Flier J S. 1997 Leptin expression and action: new experimental paradigms. Proc Natl Acad Sci USA. 94: 4242-4245.
9. Kennedy G C. 1953 The role of depot fat in the hypothalamic control of food intake in the rat. Proc R Soc. 140: 578-592.
10. Mantzoros C S. 1999 The role of leptin in human obesity and disease: a review of current evidence. Ann Intern Med. 130:671-680.
11. Brann D W, Wade M F, Dhandapani K M, Mahesh V B, Buchanan C D. 2002. Leptin and reproduction. Steroids. 67: 95-104.
12. Jope T, Lammert A, Kratzsch J, Paasch U, Glander H J. 2003 Leptin and leptin receptor in human seminal plasma and in human spermatozoa. Int J Androl 26: 335-341.
13. Sanchez-Pozo C, Rodriguez-Bano J, Dominguez-Castellano A, Muniain M A, Goberna, R, Sanchez-Margalet V. 2003 Leptinstimulates the oxidative burst in control monocytes but attenuates the oxidative burst in monocytes from HIV-infected patients. Clin Exp Immunol. 134: 464-469.
14. Maffei M, Halaas J, Ravvussin E, Prately R E, Lee G H, Zhang y, Fei H, Kim S, Lallone R, Ranganathan S, Kern P A, Friedman J M. 1995 Leptin levels in human and rodent: measurement of plasma leptin and ob RNA in obese and weight reduced subjects. Nat Med. 1: 1155-1161.

15. Blum W F, Englaro P, Hanitsch S, Jull A, Hertel N T, Muller J, Shakkebaek N E, Heiman M, Brikett M, Attanaiso A M, Kiess W, Rascher W. 1997 Plasma leptin levels in healthy children and adolescents: dependence body fat mass, gender, development stage, and testosterone. J Clin Endocrinol Metab.
16. Ostlund R E, Yang J W, Klein S, Gingerich R. 1996 Relationship between plasma leptin concentration and body fat, gender, diet, age, and metabolic covariates. J Clin Endocrinol Metab. 81: 3909-3913.
17. Mantzoros C S, Flier J S, Rogot A D. 1997 A longitudinal assessment of hormonal and physical alterations during normal puberty in boys. V. Rising leptin level may signal the onset of puberty. J Clin Endocrinol Metab. 82: 1066-1070.
18. Scholz G H, Englaro P, Thiele I, Scholz M, et al. 1996 Dissociation of serum leptin concentration and body fat content during long term dietary intervention in obese individuals. J Horm Metab Res. 28: 718-723.
19. Licinio J, Mantzoros C, Negrao A B, et al. 1997 Human leptin levels are pulsatile and inversely related to pituitary-adrenal function. Nat Med 3: 575-579.
20. Sinha M K, Ohannesian J P, Heiman M L, et al. 1996 Nocturnal rise of leptin in and non-insulin-dependent diabetes mellitus subjects. J Clin Invest. 97: 1344-1347.
21. Tartaglia L A, Dembski M, Weng X, et al. 1995 Identification and expression cloning of a leptin receptor, Ob-R. Cell 83: 1263-1271.
22. Sinha M K, Opentanova I, Ohannesian J P, Kolaczynski J W, et al. 1996 Evidence for free and bound leptin in human circulation. Studies in mean and obese subject and during short term fasting. J Clin Invest. 98: 1277-1282.
23. Maamra M, Bidlingmaier M, Postel-Vinay M C, Wu Z, Strasburger C J, Ross R J. 2001 Generation of human soluble leptin receptor by proteolytic cleavage of membrane-anchored receptors. Endocrinol. 142: 4389-4393.
24. Barbant G, Horn R, van Zur Muhlen A, Mayr B, Wurster U, Heideenreich F, et al. 2000 Free and protein bound leptin are distinct and independently controlled factors in energy regulation. Diabetologia. 43: 438-442.
25. Ma Z, Gingerich R L, Santiago J V, Klien S, Smith C H, Landt M. 1996 Radioimmunoassay of leptin in human plasma. Clin Chem. 42: 942-946.
26. Van Dielen F M H, Van T Verr C, Buurman W A, Greve J W M. 2002 Leptin and soluble leptin receptor levels in obese and weight-losing individuals. J Clin Endocrinol Metab. 87: 1708-1716.
27. Kimura E, Matsumoto K, Samori T, Kato S, Kawahara T. 2000 One-step enzyme-linked immunosorbent assay (ELISA) for measurement of serum free leptin. Clinica Chemica Acta 296: 45-57.
28. Rosenblum C I, Vangos A, Tota M R, Varnerin J P, Frazier E, Cully D F, Morsy M A, Van der Ploeg L H. 1998 A rapid, quantitative functional assay for measuring leptin. Mol Cell Endocrinol. 143: 117-123.
29. Khosravi M J, Diamandi A, Mistry J, Lee P D K. A non-competitive ELISA for human serum insulin-like growth factor-I. Clin Chem 1996; 42:1147-1154.
30. Khosravi M J, Diamandi A, Mistry J. Ultrasensitive immunoassay for prostate-specific antigen based on conventional colorimetric detection. Clin Biochem 1995; 28:407-414.
31. Khosravi J, Diamandi A, Mistry J, Krishna R G. 1999 The high molecular weight insulin-like growth factor binding protein complex: Epitope mapping, immunoassay, and preliminary clinical evaluation. J Clin Endocrinol Metab 84:2826-2833.
32. Khosravi M J, Diamandi A, Mistry J, Krishna R G, Khare A. Acid-labile subunit of human insulin-like growth factor binding protein complex: measurement, molecular, and clinical evaluation. J. Clin Endocrinol Metab 1997; 82:3944-3951.
33. A Diamandis, R G Krishna, U Bodani, N Khaja, Z Wu, C J Strasburger, J Khosravi. 2003 Soluble Leptin Receptor ELISA. The Endocrine Society 85$^{th}$ Annual Meeting.
34. Wu Z, Bidlingmaier M, Liu C, De Souza E B, Tschop M, Morrison K M, Strasburger C J. 2002 Quantification of the soluble leptin receptor in human blood by ligan-mediated immunofunctional assay. J. Clin Endocrinol Metab. 87: 2931-2939.
35. R. Janeckova. 2001 The Role of Leptin in Human Physiology and Pathophysiology. Physiol. Res. 50: 443-459.
36. Leupen, S. M. et al (1997) *Endocrinology* 138, 2735-2739.
37. Houseknecht, K. L. et al (1998) *J. Anim. Sci.* 76, 1405-1420.
38. Cohen, B. et al (1996) *Science* 274, 1185-1188.
39. Spicer, L. J. et al (1998) *Biol. Reprod.* 58, 207-212.
40. Barkan, D. et al (1999) *Endocrinology* 140, 1731-1738.
41. Sierra-Honigmann, M. R. et al (1998) *Science* 281, 1683-1686.
42. Cohen, B. et al (2001) *J. Biol. Chem.* 276, 7697-7700.
43. Almog, B. et al (2001) *Mol. Cell. Endocrinol.* 183, 179-191.
44. Roh, S. G. et al (2001) *Endocrinology* 142, 5167-5171.
45. Gertler, A. et al (1998) *FEBS Lett.* 442, 137-140.
46. Raver, N. et al (1998) *Protein Expression Purif* 14, 403-408.
47. Raver, N. et al (2000) *Protein Expression Purif* 19, 30-40.
48. Raver, N. et al (2002) *Gen. Comp. Endocrinol.* 126, 52-58.
49. Friedman, J. M. (2000) *Nature* 404, 632-634.
50. Houseknecht, K. L. et al (1998) *J. Anim. Sci.* 76, 1405-1420.
51. Campfield, L. A. et al (1996) *Horm. Metab. Res.* 28, 619-632.
52. Dridi, S. et al (2002) *Am. J. Physiol. Endocrinol. Metab.* 279, E116-E123.
53. Morrison, C. D. et al (2001) *J. Endocrinol.* 168,317-324.
54. Taouis, M. et al (2001) *Domest. Anim. Endocrinol.* 21,319-327.
55. Friedman, J. M. (2000) *Nature* 404, 632-634.
56. Houseknecht, K. L. et al (1998) *J. Anim. Sci.* 76, 1405-1420.
57. Molecular and Cellular Endocrinology 162 (2000): 95-106.
58. Fong, Mol. Pharmacol. 53:234-240.

What is claimed is:

1. A method for detecting a level of free leptin in a sample from an individual, comprising:
   contacting the sample with a chicken leptin receptor binding domain of SEQ ID NO:8 for a time sufficient to allow binding between the free leptin and the leptin receptor binding domain to form a bound complex, wherein said receptor binding domain is bound to a solid phase;
   washing the solid phase with a first wash buffer;
   contacting the solid phase with an antibody having binding specificity to leptin, wherein said antibody is coupled with a detectable label;
   washing the solid phase with a second wash buffer; and
   detecting said label remaining with said solid phase, thus detecting the level of free leptin in the sample.

2. The method of claim 1, wherein the individual is a mammal.

3. The method of claim 2, wherein said mammal is human, rat, mouse, ovine, porcine, or bovine.

4. The method of claim 1, wherein the sample is a human serum or plasma sample.

5. The method of claim 1, wherein the solid phase is a micro-titre well plate.

6. The method of claim 1, wherein the detectable label is radiolabeled, chemiluminescent, electroluminescent, fluorescent, enzyme-labeled, or bioluminescent.

7. A kit for an assay of a level of free leptin in a sample from an individual, comprising:
- a chicken leptin receptor binding domain comprising SEQ ID No. 8, wherein said domain is bound to a solid phase;
- an antibody having binding specificity for leptin; and
- a detectable label coupled with the antibody, wherein the free leptin in the sample binds to the avian leptin receptor binding domain and the antibody binds to the free leptin, thus allowing specific detection of the free leptin in the sample.

8. The kit of claim 7, wherein the individual is a mammal.

9. The kit of claim 7, wherein said mammal is human, rat, mouse, ovine, porcine, or bovine.

10. The kit of claim 7, wherein the sample is a human serum or plasma sample.

11. The kit of claim 7, wherein the solid phase is a micro-titre well plate.

12. The kit of claim 7, wherein the detectable label is radiolabeled, chemiluminescent, electroluminescent, fluorescent, enzyme-labeled, or bioluminescent.

* * * * *

SEQUENCE LISTING

<160> NUMBER OF SEQ ID NOS: 8

<210> SEQ ID NO 1
<211> LENGTH: 630
<212> TYPE: DNA
<213> ORGANISM: homo sapiens
<220> FEATURE:
<221> NAME/KEY: CDS
<222> LOCATION: (1)..(630)
<220> FEATURE:
<221> NAME/KEY: misc_feature
<222> LOCATION: (6)..(6)
<223> OTHER INFORMATION: n is a, c, g, or t

<400> SEQUENCE: 1

```
atg gcn att gat gtc aat atc aat atc tca tgt gaa act gat ggg tac       48
Met Ala Ile Asp Val Asn Ile Asn Ile Ser Cys Glu Thr Asp Gly Tyr
1               5                   10                  15 tta act aaa atg act tgc aga tgg tca acc agt aca atc cag tca ctt       96
Leu Thr Lys Met Thr Cys Arg Trp Ser Thr Ser Thr Ile Gln Ser Leu
            20                  25                  30 gcg gaa agc act ttg caa ttg agg tat cat agg agc agc ctt tac tgt      144
Ala Glu Ser Thr Leu Gln Leu Arg Tyr His Arg Ser Ser Leu Tyr Cys
        35                  40                  45 tct gat att cca tct att cat ccc ata tct gag ccc aaa gat tgc tat      192
Ser Asp Ile Pro Ser Ile His Pro Ile Ser Glu Pro Lys Asp Cys Tyr
    50                  55                  60 ttg cag agt gat ggt ttt tat gaa tgc att ttc cag cca atc ttc cta      240
Leu Gln Ser Asp Gly Phe Tyr Glu Cys Ile Phe Gln Pro Ile Phe Leu
65                  70                  75                  80 tta tct ggc tac aca atg tgg att agg atc aat cac tct cta ggt tca      288
Leu Ser Gly Tyr Thr Met Trp Ile Arg Ile Asn His Ser Leu Gly Ser
                85                  90                  95 ctt gac tct cca cca aca tgt gtc ctt cct gat tct gtg gtg aag cca      336
Leu Asp Ser Pro Pro Thr Cys Val Leu Pro Asp Ser Val Val Lys Pro
            100                 105                 110 ctg cct cca tcc agt gtg aaa gca gaa att act ata aac att gga tta      384
Leu Pro Pro Ser Ser Val Lys Ala Glu Ile Thr Ile Asn Ile Gly Leu
        115                 120                 125 ttg aaa ata tct tgg gaa aag cca gtc ttt cca gag aat aac ctt caa      432
Leu Lys Ile Ser Trp Glu Lys Pro Val Phe Pro Glu Asn Asn Leu Gln
    130                 135                 140 ttc cag att cgc tat ggt tta agt gga aaa gaa gta caa tgg aag atg      480
Phe Gln Ile Arg Tyr Gly Leu Ser Gly Lys Glu Val Gln Trp Lys Met
145                 150                 155                 160 tat gag gtt tat gat gca aaa tca aaa tct gtc agt ctc cca gtt cca      528
Tyr Glu Val Tyr Asp Ala Lys Ser Lys Ser Val Ser Leu Pro Val Pro
                165                 170                 175 gac ttg tgt gca gtc tat gct gtt cag gtg cgc tgt aag agg cta gat      576
Asp Leu Cys Ala Val Tyr Ala Val Gln Val Arg Cys Lys Arg Leu Asp
            180                 185                 190 gga ctg gga tat tgg agt aat tgg agc aat cca gcc tac aca gtt gtc      624
Gly Leu Gly Tyr Trp Ser Asn Trp Ser Asn Pro Ala Tyr Thr Val Val
        195                 200                 205 atg gat                                                               630
Met Asp
    210
```

<210> SEQ ID NO 2
<211> LENGTH: 210
<212> TYPE: PRT

<213> ORGANISM: homo sapiens

<400> SEQUENCE: 2

```
Met Ala Ile Asp Val Asn Ile Asn Ile Ser Cys Glu Thr Asp Gly Tyr
1               5                   10                  15

Leu Thr Lys Met Thr Cys Arg Trp Ser Thr Ser Thr Ile Gln Ser Leu
            20                  25                  30

Ala Glu Ser Thr Leu Gln Leu Arg Tyr His Arg Ser Ser Leu Tyr Cys
        35                  40                  45

Ser Asp Ile Pro Ser Ile His Pro Ile Ser Glu Pro Lys Asp Cys Tyr
    50                  55                  60

Leu Gln Ser Asp Gly Phe Tyr Glu Cys Ile Phe Gln Pro Ile Phe Leu
65                  70                  75                  80

Leu Ser Gly Tyr Thr Met Trp Ile Arg Ile Asn His Ser Leu Gly Ser
                85                  90                  95

Leu Asp Ser Pro Pro Thr Cys Val Leu Pro Asp Ser Val Val Lys Pro
            100                 105                 110

Leu Pro Pro Ser Ser Val Lys Ala Glu Ile Thr Ile Asn Ile Gly Leu
        115                 120                 125

Leu Lys Ile Ser Trp Glu Lys Pro Val Phe Pro Glu Asn Asn Leu Gln
130                 135                 140

Phe Gln Ile Arg Tyr Gly Leu Ser Gly Lys Glu Val Gln Trp Lys Met
145                 150                 155                 160

Tyr Glu Val Tyr Asp Ala Lys Ser Lys Ser Val Ser Leu Pro Val Pro
                165                 170                 175

Asp Leu Cys Ala Val Tyr Ala Val Gln Val Arg Cys Lys Arg Leu Asp
            180                 185                 190

Gly Leu Gly Tyr Trp Ser Asn Trp Ser Asn Pro Ala Tyr Thr Val Val
        195                 200                 205

Met Asp
    210
```

<210> SEQ ID NO 3
<211> LENGTH: 36
<212> TYPE: DNA
<213> ORGANISM: Artificial Sequence
<220> FEATURE:
<223> OTHER INFORMATION: completely synthesized

<400> SEQUENCE: 3
ggaattccat atgattgatg tcaatatcaa tatctc                                    36

<210> SEQ ID NO 4
<211> LENGTH: 39
<212> TYPE: DNA
<213> ORGANISM: Artificial Sequence
<220> FEATURE:
<223> OTHER INFORMATION: completely synthesized

<400> SEQUENCE: 4
cataggaagc tttcaatcca tgacaactgt gtaggctgg                                 39

<210> SEQ ID NO 5
<211> LENGTH: 12
<212> TYPE: PRT
<213> ORGANISM: homo sapiens
<220> FEATURE:
<221> NAME/KEY: misc_feature
<222> LOCATION: (11)..(11)
<223> OTHER INFORMATION: Xaa can be any naturally occurring amino acid

<400> SEQUENCE: 5

Met Ala Ile Asp Val Asn Ile Asn Ile Ser Xaa Glu
1               5                   10

<210> SEQ ID NO 6
<211> LENGTH: 5
<212> TYPE: PRT
<213> ORGANISM: Artificial Sequence
<220> FEATURE:
<221> NAME/KEY: misc_feature
<222> LOCATION: (3)..(3)
<223> OTHER INFORMATION: Consensus sequence, Xaa can be any naturally
      occurring amino acid

<400> SEQUENCE: 6

Trp Ser Xaa Trp Ser
1               5

<210> SEQ ID NO 7
<211> LENGTH: 627
<212> TYPE: DNA
<213> ORGANISM: gallus domesticus
<220> FEATURE:
<221> NAME/KEY: CDS
<222> LOCATION: (1)..(627)
<220> FEATURE:
<221> NAME/KEY: misc_feature
<222> LOCATION: (6)..(6)
<223> OTHER INFORMATION: n is a, c, g, or t

<400> SEQUENCE: 7

```
atg gcn gta gat gtg aat atc aat atc aaa tgt gaa act gat ggg tac      48
Met Ala Val Asp Val Asn Ile Asn Ile Lys Cys Glu Thr Asp Gly Tyr
1               5                   10                  15 tta act aaa atg act tgc aga tgg tct gca aac cca aac gca ttg ctc      96
Leu Thr Lys Met Thr Cys Arg Trp Ser Ala Asn Pro Asn Ala Leu Leu
            20                  25                  30 ttg ggg agt tcc ttg cag tta aga tac cac agg agc aaa att tat tgt    144
Leu Gly Ser Ser Leu Gln Leu Arg Tyr His Arg Ser Lys Ile Tyr Cys
        35                  40                  45 tct aac ttt cca agt act cct cca gaa tca gag gtg aaa gaa tgc cat    192
Ser Asn Phe Pro Ser Thr Pro Pro Glu Ser Glu Val Lys Glu Cys His
    50                  55                  60 ttc cag agg aat cat tct tat gag tgc aca ttt cag cct gtt ttt ctt    240
Phe Gln Arg Asn His Ser Tyr Glu Cys Thr Phe Gln Pro Val Phe Leu
65                  70                  75                  80 tta tct gga tat acc atg tgg att gag ctt aag cac tcg ctg gga aca    288
Leu Ser Gly Tyr Thr Met Trp Ile Glu Leu Lys His Ser Leu Gly Thr
                85                  90                  95 ctt gaa tcc tca cca act tgt gtc gtt cca gca gat gtg gtg aag cca    336
Leu Glu Ser Ser Pro Thr Cys Val Val Pro Ala Asp Val Val Lys Pro
            100                 105                 110 ctg cct ccc tcc aac att aaa gca gag atc acc aga aac gat ggg ctg    384
Leu Pro Pro Ser Asn Ile Lys Ala Glu Ile Thr Arg Asn Asp Gly Leu
        115                 120                 125 ctg aac gtg agc tgg aca aac ccc gtg ttt aca aat gat gac ctt aag    432
Leu Asn Val Ser Trp Thr Asn Pro Val Phe Thr Asn Asp Asp Leu Lys
    130                 135                 140 ttt cag atc cgg tac gca gtg aac agg gaa gaa ctc aca tgg gag ctg    480
Phe Gln Ile Arg Tyr Ala Val Asn Arg Glu Glu Leu Thr Trp Glu Leu
145                 150                 155                 160 tat gaa gtt cta agc gta cca aca aga tca gct gtg ata gaa gtg caa    528
Tyr Glu Val Leu Ser Val Pro Thr Arg Ser Ala Val Ile Glu Val Gln
```

-continued

```
            165                 170                 175
ctt tgt gtt gaa tat att gtt cag atc cgc tgc aga gcc ctg gat ggc      576
Leu Cys Val Glu Tyr Ile Val Gln Ile Arg Cys Arg Ala Leu Asp Gly
            180                 185                 190 tta ggc tac tgg agc aac tgg agc aga tca gcc tat gca gct gta aaa      624
Leu Gly Tyr Trp Ser Asn Trp Ser Arg Ser Ala Tyr Ala Ala Val Lys
            195                 200                 205 gat                                                                  627
Asp
```

<210> SEQ ID NO 8
<211> LENGTH: 209
<212> TYPE: PRT
<213> ORGANISM: gallus domesticus

<400> SEQUENCE: 8

```
Met Ala Val Asp Val Asn Ile Asn Ile Lys Cys Glu Thr Asp Gly Tyr
1               5                   10                  15

Leu Thr Lys Met Thr Cys Arg Trp Ser Ala Asn Pro Asn Ala Leu Leu
            20                  25                  30

Leu Gly Ser Ser Leu Gln Leu Arg Tyr His Arg Ser Lys Ile Tyr Cys
        35                  40                  45

Ser Asn Phe Pro Ser Thr Pro Pro Glu Ser Glu Val Lys Glu Cys His
    50                  55                  60

Phe Gln Arg Asn His Ser Tyr Glu Cys Thr Phe Gln Pro Val Phe Leu
65                  70                  75                  80

Leu Ser Gly Tyr Thr Met Trp Ile Glu Leu Lys His Ser Leu Gly Thr
                85                  90                  95

Leu Glu Ser Ser Pro Thr Cys Val Val Pro Ala Asp Val Lys Pro
            100                 105                 110

Leu Pro Pro Ser Asn Ile Lys Ala Glu Ile Thr Arg Asn Asp Gly Leu
        115                 120                 125

Leu Asn Val Ser Trp Thr Asn Pro Val Phe Thr Asn Asp Leu Lys
    130                 135                 140

Phe Gln Ile Arg Tyr Ala Val Asn Arg Glu Glu Leu Thr Trp Glu Leu
145                 150                 155                 160

Tyr Glu Val Leu Ser Val Pro Thr Arg Ser Ala Val Ile Glu Val Gln
                165                 170                 175

Leu Cys Val Glu Tyr Ile Val Gln Ile Arg Cys Arg Ala Leu Asp Gly
            180                 185                 190

Leu Gly Tyr Trp Ser Asn Trp Ser Arg Ser Ala Tyr Ala Ala Val Lys
        195                 200                 205

Asp
```